United States Patent
Aube et al.

(10) Patent No.: US 9,540,375 B2
(45) Date of Patent: *Jan. 10, 2017

(54) KAPPA OPIOID RECEPTOR EFFECTORS AND USES THEREOF

(71) Applicants: University of Kansas, Lawrence, KS (US); The Scripps Research Institute, Jupiter, FL (US)

(72) Inventors: Jeffrey Aube, Lawrence, KS (US); Laura Bohn, Jupiter, FL (US); Thomas Edward Prisinzano, Lawrence, KS (US); Frank John Schoenen, Lawrence, KS (US); Kevin J. Frankowski, Lawrence, KS (US)

(73) Assignees: University of Kansas, Lawrence, KS (US); The Scripps Research Institute, Jupiter, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/156,887

(22) Filed: May 17, 2016

(65) Prior Publication Data
US 2016/0257685 A1 Sep. 8, 2016

Related U.S. Application Data

(63) Continuation of application No. 14/345,273, filed as application No. PCT/US2012/055354 on Sep. 14, 2012, now Pat. No. 9,345,703.

(60) Provisional application No. 61/534,938, filed on Sep. 15, 2011.

(51) Int. Cl.
| C07D 403/14 | (2006.01) |
| C07D 249/12 | (2006.01) |
| C07D 471/14 | (2006.01) |
| A61K 31/4196 | (2006.01) |
| A61K 31/4439 | (2006.01) |
| A61K 31/444 | (2006.01) |
| A61K 31/4985 | (2006.01) |
| C07D 401/04 | (2006.01) |
| C07D 401/14 | (2006.01) |
| C07D 405/14 | (2006.01) |
| C07D 409/14 | (2006.01) |
| C07D 471/04 | (2006.01) |

(52) U.S. Cl.
CPC ......... *C07D 471/14* (2013.01); *A61K 31/4196* (2013.01); *A61K 31/444* (2013.01); *A61K 31/4439* (2013.01); *A61K 31/4985* (2013.01); *C07D 401/04* (2013.01); *C07D 401/14* (2013.01); *C07D 405/14* (2013.01); *C07D 409/14* (2013.01); *C07D 471/04* (2013.01)

(58) Field of Classification Search
CPC ............................ C07D 403/14; C07D 249/12
See application file for complete search history.

(56) References Cited

U.S. PATENT DOCUMENTS

| 5,981,543 | A | 11/1999 | Gormley et al. | 514/284 |
| 6,103,736 | A | 8/2000 | Tanaka et al. | 514/292 |
| 6,245,796 | B1 | 6/2001 | Maeno et al. | 514/403 |
| 7,294,720 | B2 | 11/2007 | Welsh et al. | 548/264.8 |
| 7,456,194 | B2 | 11/2008 | Dyckman et al. | 514/293 |
| 7,709,522 | B2 | 5/2010 | Buezo et al. | 514/429 |
| 8,642,660 | B2 | 2/2014 | Goldfarb | 514/641 |
| 2005/0209287 | A1 | 9/2005 | Olson et al. | 514/341 |
| 2006/0111348 | A1 | 5/2006 | Kampen et al. | 514/227.8 |
| 2009/0163545 | A1 | 6/2009 | Goldfarb | 514/312 |

FOREIGN PATENT DOCUMENTS

WO    WO 02/064135 A1    8/2002

OTHER PUBLICATIONS

Bruijnzeel, A.W. "Kappa-Opioid Receptor Signaling and Brain Reward Function" Brain Research Reviews 2009 62(1):127-146.
Camí, J. and Farré, M. "Drug Addiction" The New England Journal of Medicine 2003 349:975-986.
Glick et al. "Kappa Opioid Inhibition of Morphine and Cocaine Self-Administration in Rats" Brain Research 1995 681:147-152.
Hasebe et al. "Possible Pharmacotherapy of the Opioid κ Receptor Agonist for Drug Dependence" Annals of the New York Academy of Sciences 2004 1025:404-413.
Hedrick et al. "Probe Report: Agonists and Antagonists for the Kappa Opioid Receptor" MolecularLibraries Sanford Burnham Medical Research Institute 2010 AID:1785.
Hedrick et al. "Probe Report: Agonists and Antagonists for the Kappa Opioid Receptor" MolecularLibraries Sanford Burnham Medical Research Institute 2010 AID:1786.
Jones et al. "Mutational Evidence for a Common κ Antagonist Binding Pocket in the Wild-Type κ and Mutant µ [K303E] Opioid Receptors" Journal of Medicinal Chemistry 1998 41 (25):4911-4914.
McGovern et al. "CoMFA Analyses of C-2 Position Salvinorin A Analogs at the Kappa-Opioid Receptor Provides Insights Into Epimer Selectivity" Journal of Molecular Graphics and Modelling 2010 28:612-625.
Merz, H. and Stockhaus, K. "N-[(Tetrahydrofuryl)alkyl] and N-(Alkoxyalkyl) Derivatives of (−)-Normetazocine, Compounds with Differentiated Opioid Action Profiles" Journal of Medicinal Chemistry 1979 22(12):1475-1483.
Metcalf, M.D. And Coop, A. "Kappa Opioid Antagonists: Past Successes and Future Prospects" The AAPS Journal 2005 7(3):E704-E722.
Prisinzano et al. "κ Opioids as Potential Treatments for Stimulant Dependence" The AAPS Journal 2005 7(3):E592-E599.
Roth et al. "Salvinorin A: a Potent Naturally Occurring Non-nitrogenous κ Opioid Selective Agonist" Proceedings of the National Academy of Sciences 2002 99(18):11934-11939.

(Continued)

*Primary Examiner* — Bruck Kifle
(74) *Attorney, Agent, or Firm* — Licata & Tyrrell P.C.

(57) ABSTRACT

The present invention is a selective kappa opioid receptor effector, or a pharmaceutically acceptable salt thereof, useful for treating ethanol use disorder withdrawal, anxiety and/or depression, schizophrenia, mania or post-traumatic stress disorder.

2 Claims, 1 Drawing Sheet

(56) References Cited

OTHER PUBLICATIONS

Szmuszkovicz, J. and VonVoigtlander, P.F. "Benzeneacetamide Amines: Structurally Novel Non-mµ Opioids" Journal of Medicinal Chemistry 1982 25:1125-1126.

Thomas et al. "Identification of the First *trans*-(3R,4R)-Dimethyl-4-(3-hydroxyphenyl) piperidine Derivative to Possess Highly Potent and Selective Opioid κ Receptor Antagonist Activity" Journal of Medicinal Chemistry 2001 44:2687-2690.

Xuei et al. "Association of the κ-Opioid System with Alcohol Dependence" Molecular Psychiatry 2006 11:1016-1024.

International Search Report from PCT/US2012/055354, Jan. 22, 2013, PCT.

International Preliminary Report on Patentability from PCT/US2012/055354, Mar. 18, 2014, PCT.

PubChem BioAssay: AID 488925 "Sar Analysis of Antagonists of the Kappa Opioid Receptor (KOR) Using an Image-Based Assay—Set 4" XP-002729105 May 3, 2011.

PubChem BioAssay: AID 434981 "Sar Analysis of Small Molecule Antagonists of the Kappa Opioid Receptor via a Luminescent Beta-Arrestin Assay—Set 3" XP-002729106 May 3, 2011.

PubChem BioAssay: AID 449737 "Sar Analysis of Small Molecule Antagonists of the Kappa Opioid Receptor via a Luminescent Beta-Arrestin Assay—Set 3" XP-002729107 Jan. 14, 2011.

PubChem BioAssay: AID 1786 "Summary of Small Molecule Agonists of the Kappa Opioid Receptor" XP-002729108 Jan. 4, 2011.

PubChem BioAssay: AID 2497 "Sar Analysis of Agonists of the Kappa Opioid Receptor (KOR) Using an Image-Based Assay—Set 2" XP-002729109 Jan. 13, 2011.

Frankowski et al. "Discovery of Small Molecule Kappa Opioid Receptor Agonist and Antagonist Chemotypes through a HTS and Hit Refinement Strategy" ACS Chemical Neuroscience 2012 3(2): 221-236.

McGovern et al. "CoMFA Analyses of C-2 Position Salvinorin A Analogs at the Kappa-Opioid Receptor Provides Insights into Epimer Selectivity" Journal of Molecular Graphics and Modelling 2010 28(7) :612-625.

Supplementary Search Report from EP 12831982.9, Oct. 10, 2014, EP.

Di Grandi et al. "Small molecule inhibitors of HIV RT Riponucloease H" Bioorganic & Medicinal Chemistry Letters 2010 20:398-402.

Office Communication dated Nov. 28, 2014 from U.S. Appl. No. 14/345,273, filed Mar. 17, 2014.

Office Communication dated May 13, 2015 from U.S. Appl. No. 14/345,273, filed Mar. 17, 2014.

Office Communication dated Nov. 4, 2015 from U.S. Appl. No. 14/345,273, filed Mar. 17, 2014.

Office Communication dated Feb. 19, 2016 from U.S. Appl. No. 14/345,273, filed Mar. 17, 2014.

KAPPA OPIOID RECEPTOR EFFECTORS AND USES THEREOF

INTRODUCTION

This application is a continuation of U.S. Ser. No. 14/345,273 filed Mar. 17, 2014 which is the national phase application of PCT/US2012/055354 filed Sep. 14, 2012 which claims the benefit of priority of U.S. Provisional Application No. 61/534,938, filed Sep. 15, 2011, the contents of which are incorporated herein by reference in their entirety.

This invention was made with government support under Grant Nos. R01 DA031927 and U54 HG005031 awarded by the National Institutes of Health. The government has certain rights in the invention.

BACKGROUND OF THE INVENTION

For normal activities that produce rewards, there is a rapid habituation of the circuits involved and the behaviors will wane. However, for addictive drugs habituation does not occur and dopamine release persists despite repetitive trials. Upon withdrawal of the drug, a decrease of dopamine levels in the nucleus accumbens results, and this has been observed for opioids, cannabinoids, alcohol, amphetamines, and nicotine (Cami & Farre (2003) *N. Engl. J. Med.* 349:975). This loss of dopamine accounts for the withdrawal syndromes observed with these drugs. The prototype opioid drug is morphine. It produces many effects typical of most opioids including analgesia, euphoria, nausea, and respiratory depression. Repeated use of opioids produces physical dependence and tolerance. These manifestations of opioid use are due to the three recognized types of opioid receptors that are members of the GPCR family, the mu (μ), delta (δ), and kappa (κ) subtype receptors. While stimulation of the mu and delta receptors increases dopamine release in the nucleus accumbens, κ opioid (KOP) receptor activation by its endogenous ligand dynorphin-A reduces extracellular dopamine. It has been suggested that stimulation of KOP receptor by endogenous opioids like dynorphins will produce an aversive state and thereby counter the effects of rewarding and addictive compounds like alcohol, cocaine and nicotine. Moreover, exogenous KOR agonists have also been observed to attenuate drug-taking behavior (Prisinzano, et al. (2005) *AAPS J.* 7:E592; Xuei, et al. (2006) *Mol. Psychiatry* 11:1016; Hasebe, et al. (2004) *Ann. NY Acad. Sci.* 1025:404; Metcalf & Coop (2005) *AAPS J.* 7:E704). However, it may be difficult to strike a balance between opposing the sense of reward gained by drugs of abuse and producing an aversive state; therefore, activation of the KOP receptor may not be therapeutically preferable. Although these statements appear contrary, KOP receptor agonists can both alleviate drug self-administration in animal models (most likely via dopamine regulation) and also trigger relapse. This conflicting dual action of KOP receptor agonists alludes to the complex physiological role of KOP receptors and underscores the need for a variety of chemical tools to facilitate their further investigation.

Intracranial self-stimulation has become a useful means of assessing reward thresholds in rodents and nonhuman primates. In essence, an animal will press a lever to electrically stimulate the brain via implanted probes. This "self stimulation" will be performed to a certain extent in training and that extent is an indication of the animal's "reward threshold." Administration of "drugs of abuse" has been shown to decrease this reward threshold such that the animal will seek less stimulation to achieve the desired effect. This model paradigm has been likened to positive hedonic states produced by drugs of abuse in human addicts. In rodents, the direct activation of KOP receptor using selective agonists increases reward thresholds (mimicking the withdrawal state) and creating a "depressive-like" state (where more self stimulation is required to achieve the desired effect). Treatment with antagonists has been shown to restore reward thresholds in this model (Glick, et al. (1995) *Brain Res.* 681:147; Bruijnzeel (2009) *Brain Res. Rev.* 62:127). The restoration of reward thresholds may be a very important step in drug abuse treatment as drug cessation is strongly negatively reinforced by aversive feelings, which may be due to an increased reward threshold. Therefore, the development of KOP receptor antagonists would be particularly beneficial in "resetting" this threshold. Furthermore, since an increased reward threshold may manifest as a "depressive state," then KOP receptor antagonists can also be beneficial for the treatment of depressive disorders.

There are molecules known to activate or inhibit the KOP receptor, including salvinorin A, ketazocine, U-50,488, 5'-guanidinonaltrindole and JDTic ((3R)-7-Hydroxy-N-((1S)-1-[[(3R,4R)-4-(3-hydroxyphenyl)-3,4-dimethyl-1-piperidinyl]methyl]-2-methylpropyl)-1,2,3,4-tetrahydro-3-isoquinolinecarboxamide). Many of these molecules are either direct derivatives of opium alkaloids such as GNTI (5'-guanidinyl-17-(cyclopropylmethyl)-6,7-dehydro-4,5alpha-epoxy-3,14-dihydroxy-6,7-2',3'-indolomorphinan; Jones, et al. (1998) *J. Med. Chem.* 41:4911) or contain structural elements borrowed from these alkaloids, as can be observed for JDTic (Thomas, et al. (2001) *J. Med. Chem.* 44:2687-2690) and ketazocine (Merz & Stockhaus (1979) *J. Med. Chem.* 22:1475-1483). One consequence of this legacy is that many of the established potent and selective molecules are structurally complex, containing multiple stereocenters and requiring lengthy synthetic routes to construct modified analogues. The natural product Salvinorin A (Roth, et al. (2002) *Proc. Natl. Acad. Sci. U.S.A.* 99:11934-11939) is unique as a potent, non-nitrogenous KOP receptor ligand. While not an alkaloid, Salvinorin A is equal in structural complexity to any of the isolated opiates. Even the widely utilized, simplified agonist compound, U-50,488 (VonVoigtlander & Szmuszkovicz (1982) *J. Med. Chem.* 25:1125-1126) contains two chiral centers.

Currently, there are currently no approved agents or compounds for treating the altered reward pathways associated with drug addiction (Prisinzano (2005) supra). Accordingly, there is a need in the art for effector chemotypes (possessing novel patterns of binding toward the KOP receptor) that can be readily synthesized for use in analyzing the KOP receptor as well as in therapeutic methods.

SUMMARY OF THE INVENTION

The present invention is a pharmaceutical composition containing an effective amount of a kappa opioid receptor antagonist, or a pharmaceutically acceptable salt thereof, and a physiologically acceptable carrier, wherein the kappa opioid receptor antagonist is a compound of Formula I:

Formula I

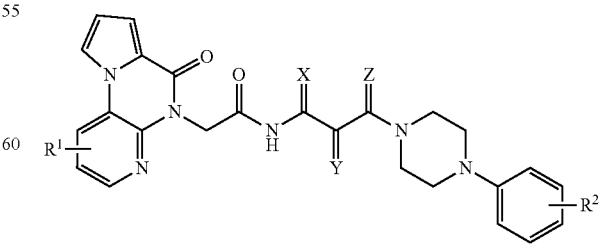

wherein
X, Y and Z are independently selected from H, H; O; S or NH;

$R^1$ is H, a halogen group or a substituted or unsubstituted lower alkyl or alkoxy group; and $R^2$ is present or absent, and when present is a substituent on one or more ring atoms and is for each ring atom independently H, a halogen group, or a substituted or unsubstituted lower alkyl or alkoxy group. In some embodiments, the pharmaceutical composition further includes a kappa opioid receptor agonist.

The present invention also provides a pharmaceutical composition containing an effective amount of a kappa opioid receptor agonist, or a pharmaceutically acceptable salt thereof, and a physiologically acceptable carrier, wherein the kappa opioid receptor agonist is a compound of Formula II:

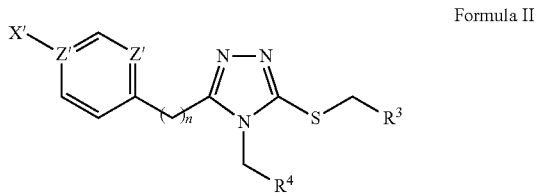

Formula II wherein
X' is hydrogen or Br;
each Z' is independently C, CH or N;
n is 0 or 1;
$R^3$ is phenyl, substituted phenyl, naphthyl, cycloalkyl, propargyl or allyl; and
$R^4$ is aryl, heteroaryl or cycloalkyl. In particular embodiments, $R^4$ is 2-furyl, 2-thiophene or 3-pyridyl.

Methods of using the kappa opioid receptor antagonist or agonist to selectively modulate the activity of kappa opioid receptor in vitro and in the treatment of a patient with, e.g., an ethanol use disorder, an anxiety disorder, a depressive illness, schizophrenia, mania or post-traumatic stress disorder are also provided.

DETAILED DESCRIPTION OF THE INVENTION

Figure 1A:
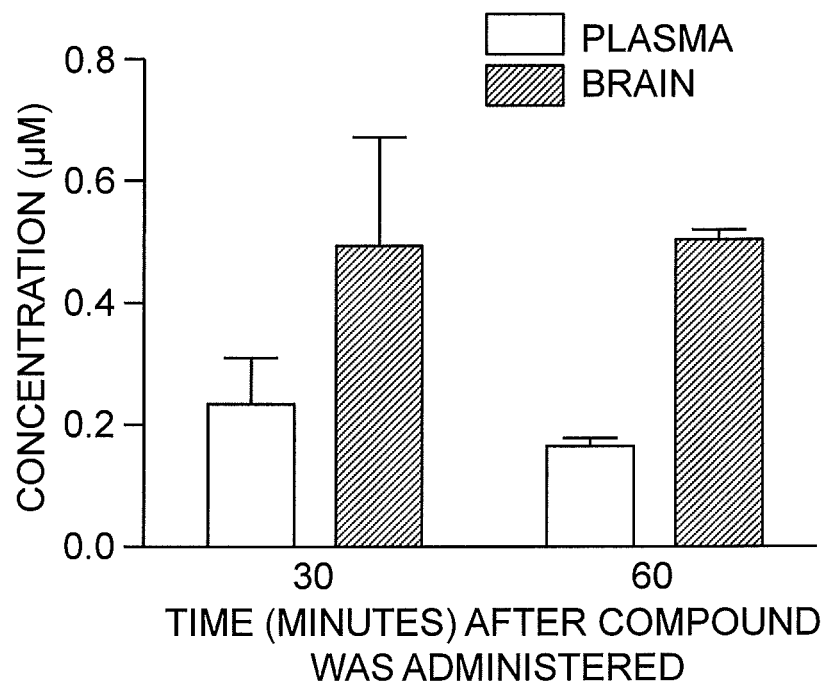
FIG. 1A AND FIG. 1B show plasma and brain concentrations of two representative triazole analogues (KUIP10051N, FIG. 1A; and KUC1404186N, FIG. 1B) administered to 2 month old mice (10 mg/kg, i.p.). Plasma and brains were collected at 30 and 60 minutes from two groups of mice (n=3). Concentrations were determined from standard curves prepared in the appropriate matrix. Presented are the calculated means±SEM.

Using a high throughput screening (HTS) campaign and subsequent hit optimization, new effector (antagonist and agonist) chemotypes of the KOP receptor (KOR) have now been developed. These distinct classes of KOR ligands were developed based on initial hit compounds and subsequent optimization through the synthesis of additional analogues to investigate the Structure-Activity Relationship (SAR).

KOR Antagonists.

When compared with known KOR antagonists such as 5'-guanidinonaltrindole and JDTic, the instant pyridopyrrolo pyrazinone antagonist (Chemotype I, Formula I) is unique with a simplified, modular structure.

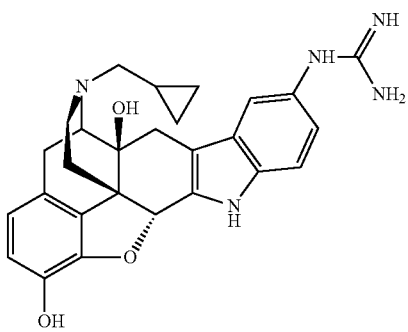

5'-guanidinonaltrindole

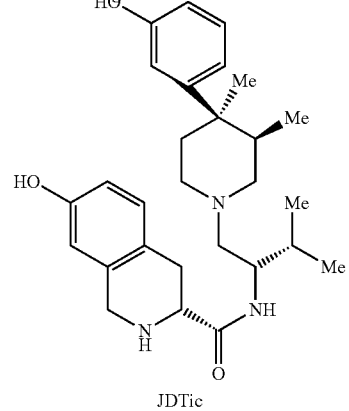

JDTic

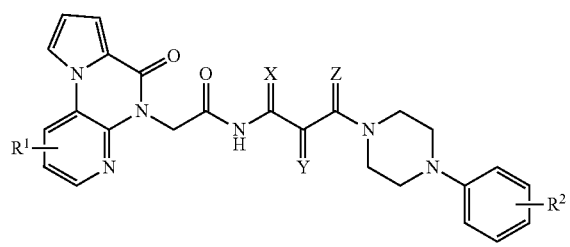

Formula I

This chemotype of KOR antagonists is of use in selectively inhibiting the human kappa opioid receptor to provide a scientific tool useful in helping to elucidate individual brain pathways that underlie addictive behavior, thus enabling improved understanding of the molecular basis of dependency and potentially providing a basis for therapeutic development. Moreover, given that the instant compounds are in the range of potencies for administration to animals, these antagonists, as well as analogs and derivatives therefore find use in the treatment of addiction, prevention of reinstatement of drug taking behavior, blocking aspects of nicotine withdrawal, and treatment of depression and post-traumatic stress disorder (PTSD).

Accordingly, the present invention provides kappa opioid antagonists that bind to kappa opioid receptors with high affinity and/or specificity. Antagonists of the present invention are those represented by the Formula I:

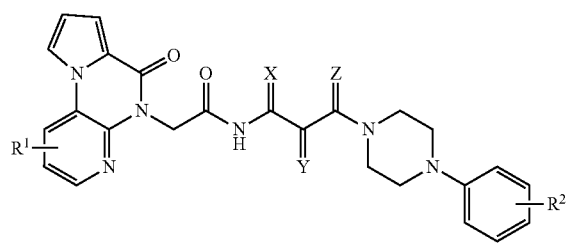

Formula I wherein

X, Y and Z are independently selected from H, H; O; S or NH;

R¹ is H, a halogen group (e.g., F, I, Cl or Br), or a substituted or unsubstituted lower alkyl or alkoxy group; and R² is present or absent, and when present is a substituent on one or more ring atoms (e.g., position 2, 3, or 4) and is for each ring atom independently H, a halogen group, or a substituted or unsubstituted lower alkyl or alkoxy group.

KOR Agonists.

The structure of the instant agonists of Chemotype II (Formula II) are distinct from known KOR agonists such as Salvinorin A, Ketazocine and U-50488.

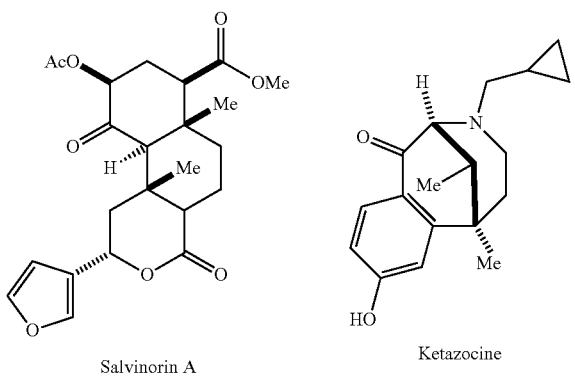

Salvinorin A

Ketazocine

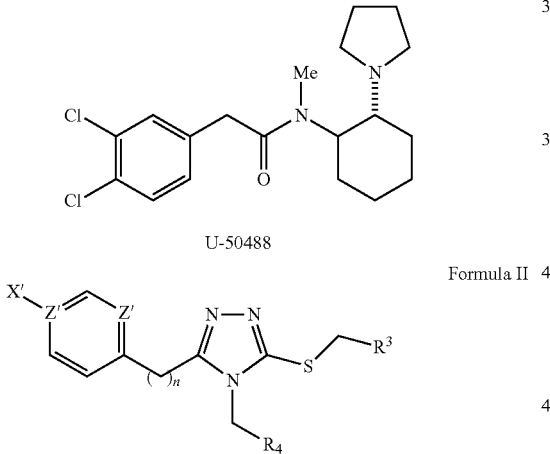

U-50488

Formula II

Evidence indicates that activation of KOR opposes a variety of MOR-mediated actions throughout the brain and spinal cord (Pan (1998) *Trends Pharmacol. Sci.* 19(3):94-8). Studies indicate that antagonism of endogenous KOR apparently elicits a potentiating effect on some morphine-withdrawal signs, including weight loss. Stimulation of endogenous KOR is therefore of use in attenuating morphine withdrawal symptoms. In this respect, Dynorphin A, a know KOR agonist, has been reported to inhibit morphine withdrawal symptoms induced by naloxone precipitation or morphine discontinuation in morphine-dependent animals (Suzuki, et al. (1992) *Life Sci.*, 50(12):849-56). Therefore, not only is Chemotype II of use as a scientific tool to elucidate individual brain pathways that underlie addictive behavior, these agonists are useful in the treatment of withdrawal. Moreover, the instant agonists, as well as analogs, derivatives and partial agonists therefore, find use in the treatment of the manic phase of bipolar disorder, among other conditions.

Accordingly, the present invention provides kappa opioid agonists that bind to kappa opioid receptors with high affinity and/or specificity. Agonist compounds of the present invention are those represented by the Formula II:

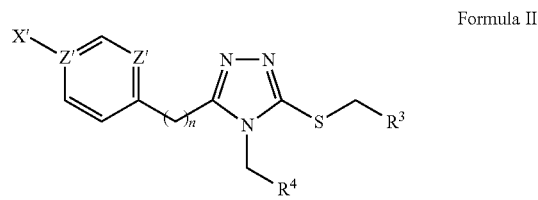

Formula II wherein

X' is hydrogen or Br;

each Z' is independently C, CH or N;

n is 0 or 1;

R³ is phenyl, substituted phenyl, naphthyl, cycloalkyl, propargyl or allyl; and

R⁴ is aryl, heteroaryl or cycloalkyl. In particular embodiments, R⁴ is 2-furyl, 2-thiophene or 3-pyridyl.

For the compounds of this invention, the term "lower alkyl" is intended to mean a branched or unbranched saturated monovalent hydrocarbon radical containing 1 to 6 carbon atoms, such as methyl, ethyl, propyl, isopropyl, tert-butyl, butyl, n-hexyl and the like. Similarly, a lower alkoxy group is a C1-C6 alkoxy group, such as methoxy, ethoxy, or acetoxy.

"Cycloalkyl" means a monocyclic or fused bicyclic, saturated or partially unsaturated, monovalent hydrocarbon radical of three to ten carbon ring atoms. Unless otherwise stated, the valency of the group may be located on any atom of any ring within the radical, valency rules permitting. More specifically, the term cycloalkyl includes, but is not limited to, cyclopropyl, cyclobutyl, cyclopentyl, cyclohexyl, decahydronaphthyl (including, but not limited to decahydronaphth-1-yl, decahydronaphth-2-yl, and the like), norbornyl, adamantly, or cyclohexenyl, and the like. The cycloalkyl ring may be unsubstituted or substituted with one or more substituents which may be the same or different, and are as defined herein.

The term "aryl" refers to single-ring aromatic radicals which may include from 5 to 20 carbon atoms. Aryl groups include, but are not limited to, phenyl, biphenyl, anthracenyl, and naphthenyl. The phrase "substituted aryl group" refers to an aryl group that is substituted with one or more substituents.

The phrase "heteroaryl" refers to a 3 to 20-membered aromatic ring composed of carbon atoms and heteroatoms, such as N, S, and O. The heteroaryl ring may be attached at any heteroatom or carbon atom. Representative heteroaryl compounds include, for example, imidazolyl, pyridyl, pyrazinyl, pyrimidinyl, thiophenyl, thiazolyl, furanyl, pyridofuranyl, pyrimidofuranyl, pyridothienyl, pyridazothienyl, pyridooxazolyl, pyridazooxazolyl, pyrimidooxazolyl, pyridothiazolyl, pyridazothiazolyl, pyrrolyl, pyrrolinyl, imidazolyl, pyrazolyl, pyridyl, dihydropyridyl, pyrimidyl, pyrazinyl, pyridazinyl, triazolyl (e.g., 4H-1,2,4-triazolyl, 1H-1,2,3-triazolyl, and 2H-1,2,3-triazolyl), tetrazolyl, (e.g., 1H-tetrazolyl and 2H tetrazolyl), pyrrolidinyl, imidazolidinyl, piperidinyl, piperazinyl, indolyl, isoindolyl, indolinyl, indolizinyl, benzimidazolyl, quinolyl, isoquinolyl, indazolyl, benzotriazolyl, oxazolyl, isoxazolyl, oxadiazolyl (e.g., 1,2,4-oxadiazolyl, 1,3,4-oxadiazolyl, and 1,2,5-oxadiazolyl), benzoxazolyl, benzoxadiazolyl, benzoxazinyl (e.g., 2H-1,4-benzoxazinyl), thiazolyl, isothiazolyl, thiadiazolyl (e.g., 1,2,3-thiadiazolyl, 1,2,4-thiadiazolyl, 1,3,4-thiadiazolyl, and 1,2,5-thiadiazolyl). The phrase "substituted heteroaryl" refers to a heteroaryl group that is substituted with one or more substituents.

Exemplary substituent groups of lower alkyl, alkoxy, cycloalkyl, aryl, phenyl and heteroaryl groups include, but are not limited to, one or more halogen groups (i.e., fluorine, chlorine, bromine and iodine), lower alkyl groups, lower alkoxy groups, alkenyl groups (e.g., C2-C6), hydroxyl groups, amine groups, amide groups, nitro groups, nitroso groups, aldehyde groups, carboxyl groups, sulhydryl groups, =O, —$CF_3$, —CN, and carbonothioyl groups.

The antagonist and agonist compounds of the present invention, including analogs, derivatives and partial agonists thereof, are selective for the kappa receptor. By "selective kappa antagonist" is meant any chemical compound which has affinity for the kappa opioid receptor, substantially no agonist activity, and produces less than 15% of the maximal response in comparison to dynorphin A. The selective kappa antagonist has more than 5, 10, 25, 50, 100, 200, 300, 500, 700, 1,000, or 2,000 fold greater affinity for kappa opioid receptors than for each of the mu and delta opioid receptors. Affinities for the various opioid receptor subtypes are determined using standard in vitro assays. For example, the binding assays may be conducted as described herein or may utilize guinea pig brain membranes or stably transfected Chinese Hamster Ovary (CHO) cells expressing each of the three opioid receptors. In particular embodiments, the instant compounds are specific for the kappa opioid receptor and exhibit greater than 100-fold affinity over the mu opioid receptor and 10-fold affinity over the delta opioid receptor.

By "selective kappa receptor partial agonist" is meant a chemical compound which has affinity for the kappa opioid receptor and exhibits agonist activity, but produces only a partial (i.e., submaximal) response of between 15% and 85% in comparison to dynorphin A, an endogenous neurotransmitter of the kappa opioid receptor. The selective kappa partial agonist has more than 5, 10, 25, 50, 100, 200, 300, 500, 700, 1,000, or 2,000 fold greater affinity for kappa opioid receptors than for each of the mu and delta opioid receptors.

By "selective kappa receptor agonist" is meant a chemical compound which has affinity for the kappa opioid receptor, exhibits agonist activity, and produces at least 85% of the maximal response in comparison to dynorphin A. The selective kappa agonist has more than 5, 10, 25, 50, 100, 200, 300, 500, 700, 1,000, or 2,000 fold greater affinity for kappa opioid receptors than for each of the mu and delta opioid receptors.

A most preferred set of antagonist compounds of Formula I includes the compounds as shown in Table 1. A most preferred set of agonist compounds of Formula II includes the compounds as shown in Table 8. Such compounds can be prepared as pharmaceutical compositions, pharmaceutically acceptable derivatives, or pharmaceutically acceptable salts and be provided alone or in combination in the form of a kit with unit doses of the subject compounds. In such kits, in addition to the containers containing the unit doses will be an informational package insert describing the use and attendant benefits of using the compound(s).

A "pharmaceutically acceptable derivative" of a compound of the invention include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs.

A "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

In addition to the compounds specifically disclosed herein, the present invention also pertains to analogs, derivatives and partial agonists of said compounds that modulate (i.e., agonize or antagonize) KOR activity. Broadly, the KOR three-dimensional crystal structure in combination with the structure of the instant compounds can be used to design or screen for a test compound with KOR modulatory activity; and the compound designed or screened for can be tested for its ability to selectively agonize or antagonize the activity of KOR.

The receptor selectivities discussed above are determined based on the binding affinities at the receptors indicated or their selectivity in opioid functional assays exemplified herein including, but not limited to a [$^{35}$S]GTPγ-S assay, the DISCOVERX PATHHUNTER β-arrestin recruitment assay and/or a high content imaging β-arrestin translocation assay.

The compounds of the present invention can be used to bind kappa opioid receptors. Such binding can be accomplished by contacting the receptor with an effective amount of the inventive compound. Of course, such contacting is preferably conducted in an aqueous medium, preferably at physiologically relevant ionic strength, pH, etc.

The inventive compounds can also be used to treat patients having disease states which are ameliorated by binding opioid receptors or in any treatment wherein temporary suppression or activation of the kappa opioid receptor system is desired. Specifically, kappa opioid receptor antagonists are of use in the treatment of opiate addiction (such as heroin addiction), or cocaine addiction as well as being useful as cytostatic agents, as anti-migraine agents, as immunomodulators, as immunosuppressives, as antiarthritic agents, as anti-allergic agents, as virucides, to treat diarrhea, as antipsychotics, as anti-schizophrenics, as anti-depressants, as uropathic agents, as antitussives, as anti-addictive agents, as anti-smoking agents, to treat alcoholism, as hypotensive agents, to treat and/or prevent paralysis resulting from traumatic ischemia, general neuroprotection against ischemic trauma, as adjuncts to nerve growth factor treatment of hyperalgesia and nerve grafts, as anti-diuretics, as stimulants, as anti-convulsants, or to treat obesity. Additionally, the present antagonists can be used in the treatment of Parkinson's disease as an adjunct to L-dopa for treatment of dyskinesia associated with the L-dopa treatment. They can also be used with kappa agonists disclosed herein or those known in the art (e.g., U-50,488, Salvinorin A, and Ketazocine) as analgesics, or for any condition requiring suppression of the kappa receptor system. Selective kappa receptor agonists of the invention are particularly useful for treating mania associated with bipolar disorder, acute mania, and chronic mania.

Post-traumatic Stress Disorder (PTSD) is an anxiety disorder that can develop after exposure to a traumatic event. Emerging evidence suggests that opiate systems may modulate the development and expression of PTSD. Mu opioid receptor (MOR) analgesics, such as morphine, are often given as a response to trauma, and there is emerging evidence that they are, at least partially, protective against PTSD. The kappa opioid receptor (KOR) system has also been implicated in stress-related processes, with KOR agonists reported to enhance stress in both laboratory animals and in humans, and KOR antagonists reported to attenuate stress-like behaviors. Therefore, the KOR antagonists of this invention also find use in the treatment of trauma and in reducing the emergence and persistence of PTSD.

As used herein, the term "subject" or "patient" is intended to include living organisms in which certain conditions as described herein can occur. Examples include humans, monkeys, cows, sheep, goats, dogs, cats, mice, rats, and transgenic species thereof. In a particular embodiment, the subject is a primate. In a specific embodiment, the primate is a human. Other examples of subjects include experimental animals such as mice, rats, dogs, cats, goats, sheep, pigs, and cows. The experimental animal can be an animal model for a disorder, e.g., a transgenic mouse with an Alzheimer's-type neuropathology.

The compounds of the present invention can be administered in an effective amount by any of the conventional techniques well-established in the medical field. For example, the compounds can be administered orally, intravenously, or intramuscularly. When so administered, the inventive compounds can be combined with any of the well-known pharmaceutical carriers and additives that are customarily used in such pharmaceutical compositions. For a discussion of dosing forms, carriers, additives, pharmacodynamics, etc., see Kirk-Othmer Encyclopedia of Chemical Technology, Fourth Edition, Vol. 18, 1996, pp. 480-590. The patient is preferably a mammal, with human patients especially preferred. Effective amounts are readily determined by those of ordinary skill in the art.

Active compounds are administered at a therapeutically effective dosage sufficient to treat a subject. An "effective amount" desirably reduces the amount of symptoms of the condition in the subject by at least about 20%, more preferably by at least about 40%, even more preferably by at least about 60%, and still more preferably by at least about 80% relative to untreated subjects. For example, the efficacy of a compound can be evaluated in an animal model system that is predictive of efficacy in treating the disease in humans.

Compounds of this invention can be administered as a single dosage per day, or as multiple dosages per day. When administered as multiple dosages, the dosages can be equal doses or doses of varying amount, based upon the time between the doses (i.e., when there will be a longer time between doses, such as overnight while sleeping, the dose administered will be higher to allow the compound to be present in the bloodstream of the patient for the longer period of time at effective levels). Preferably, the compound and compositions containing the compound are administered as a single dose or from 2-4 equal doses per day.

Pharmaceutical compositions containing the present compounds typically include a physiologically acceptable carrier, such as buffer or conventional pharmaceutical solid carriers, and if desired, one or more other excipients.

The invention is described in greater detail by the following non-limiting examples.

Example 1

Screening and Hit Identification

The distinct class of KOR ligands presented herein was developed based on initial hit compounds uncovered through the screening of the Molecular Libraries Small Molecule Repository (MLSMR) compound collection and subsequent optimization through the synthesis of additional analogues to investigate SAR. The project was initiated to develop new chemical probes and it was contemplated that the interest in elucidating the pharmacology of the KOR would benefit from a diverse collection of readily-available ligands. Ideally, these ligands would possess a range of pharmacological profiles. For a compound to be interesting as a lead for a pharmacological probe, it must be selective for the KOR over the other opioid receptors and possess sufficient potency to be useful. It was determined that a 100-fold selectivity and 1 µM potency was the minimum criteria for an interesting lead compound of each chemotype. Moreover, any new chemotype could not resemble any already known opioid ligand. Based on these requirements, MLPCN probe antagonist compounds were analyzed (Hedrick, et al. Selective KOP receptor agonists, PMID: 21433386, PUBCHEM AID 1786; Hedrick, et al. Selective KOP receptor antagonists, PMID: 21433381, PUBCHEM AID 1785).

In this campaign, two assay platforms were employed to evaluate KOR activity and selectivity: the KOR1 DISCOVERX β-Arrestin PATHHUNTER assay and an imaging based β-arrestin translocation assay for confirmatory and selectivity assays. The KOR1 DISCOVERX β-Arrestin PATHHUNTER assay is a commercial platform for direct measurement of GPCR (G protein-coupled receptor) activation by detection of β-Arrestin binding to the KOR. In this system, β-Arrestin is fused to an N-terminal deletion mutant of β-galactosidase (termed the enzyme acceptor or EA) and the GPCR of interest is fused to a smaller (42 amino acid), weakly complementing fragment (termed PROLINK). In cells that stably express these fusion proteins, ligand stimulation results in the recruitment of β-Arrestin by the GPCR. This interaction encourages the complementation of the two β-galactosidase fragments resulting in the formation of a functional enzyme that converts substrate in the assay medium to a detectable signal. The imaging based high-content β-arrestin translocation assay is based upon the redistribution of β-Arrestin linked to green fluorescent protein (GFP) to the cell surface and detection (Barak, et al. (1997) *J. Biol. Chem.* 272:27497-27500).

The minimum criteria for a successful probe compound were set as an $IC_{50}$ of less than 1 µM in the KOR1 DISCOVERX β-Arrestin assay and greater than 100-fold selective for the KOR over either the MOR (mu opioid receptor) or DOR (delta opioid receptor) in the β-arrestin translocation comparison assay (or within the detection limits of the assay platform). Moreover, it was of importance to identify KOR agonists and antagonists different from probes known in the art, as well as scaffolds that would be chemically attractive in terms of synthetic accessibility and structural malleability.

Initially, a portion (approximately 290,000 compounds) of the MLSMR compound collection was tested in the KOR1 DISCOVERX β-arrestin primary kappa opioid (KOP) agonist and antagonist screens (PUBCHEM AID 1777 and 1778, respectively) at a single concentration point (10 μM). Compounds with an activity >50% were retested with compound solutions resupplied from the MLSMR collection to confirm single concentration activity. The confirmed compounds were further tested in concentration response screens using the DISCOVERX β-arrestin primary KOP agonist and antagonist screen to obtain $EC_{50}$ or $IC_{50}$ values (PUBCHEM AID 2284 and 2285, respectively). These compounds were concurrently tested in a β-galactosidase counterscreen assay (PUBCHEM AID 1966) to assess the possibility that these compounds might inhibit the reporting enzyme. The activity of the validated compounds was confirmed in the KOR agonist and antagonist β-arrestin translocation assay (PUBCHEM AID 2359 and 2348, respectively). The KOR:DOR:MOR selectivity of the compounds was determined using the analogous β-arrestin translocation assays for the DOR (PUBCHEM AID 2370 and 2357, for agonists and antagonist, respectively) and the MOR (PUBCHEM AID 2352 and 2420, for agonists and antagonists, respectively). The minimum threshold for the identification of an interesting new chemotype was set as an $IC_H$ (agonist) or $EC_{50}$ (antagonist) of less than 1 μM in the KOR PATHHUNTER assay and greater than 100-fold selective for the KOR over either the MOR or DOR in the β-arrestin translocation assay (or within the detection limits of the assay platform). Following data analysis and attrition of compounds from the counterscreen, novel and selective classes of compounds emerged from the screens possessing a strong potential for optimization. The chemotype (Chemotype I) of antagonistic compounds was based upon the representative achiral compound, N—N-(3-(4-(4-methoxyphenyl)piperazin-1-yl)propyl)-2-(1-methyl-6-oxopyrido[2,3-e]pyrrolo[1,2-a]pyrazin-5(6H)-yl)acetamide (PUBCHEM Compound ID 44665680, Substance ID 88442997), referred to herein as compound 1{3}.

The chemotype (Chemotype II) of agonistic compounds was based upon the following representative compound, referred to herein as compound 2{6} (PUBCHEM Compound ID 2482316, Substance ID 17388459).

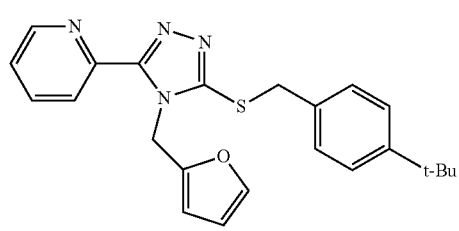 [SMILES: CC(C)(C)c1ccc(CSc2nnc(-c3ccccn3)n2Cc2ccco2)cc1]

Example 2

Synthesis of Compound 1{3}

Compound 1{3} was readily synthesized by the synthetic route shown in Scheme 1. Of particular note, compound 1{3} is achiral, which is in contrast to conventional KOR antagonists.

SCHEME 1

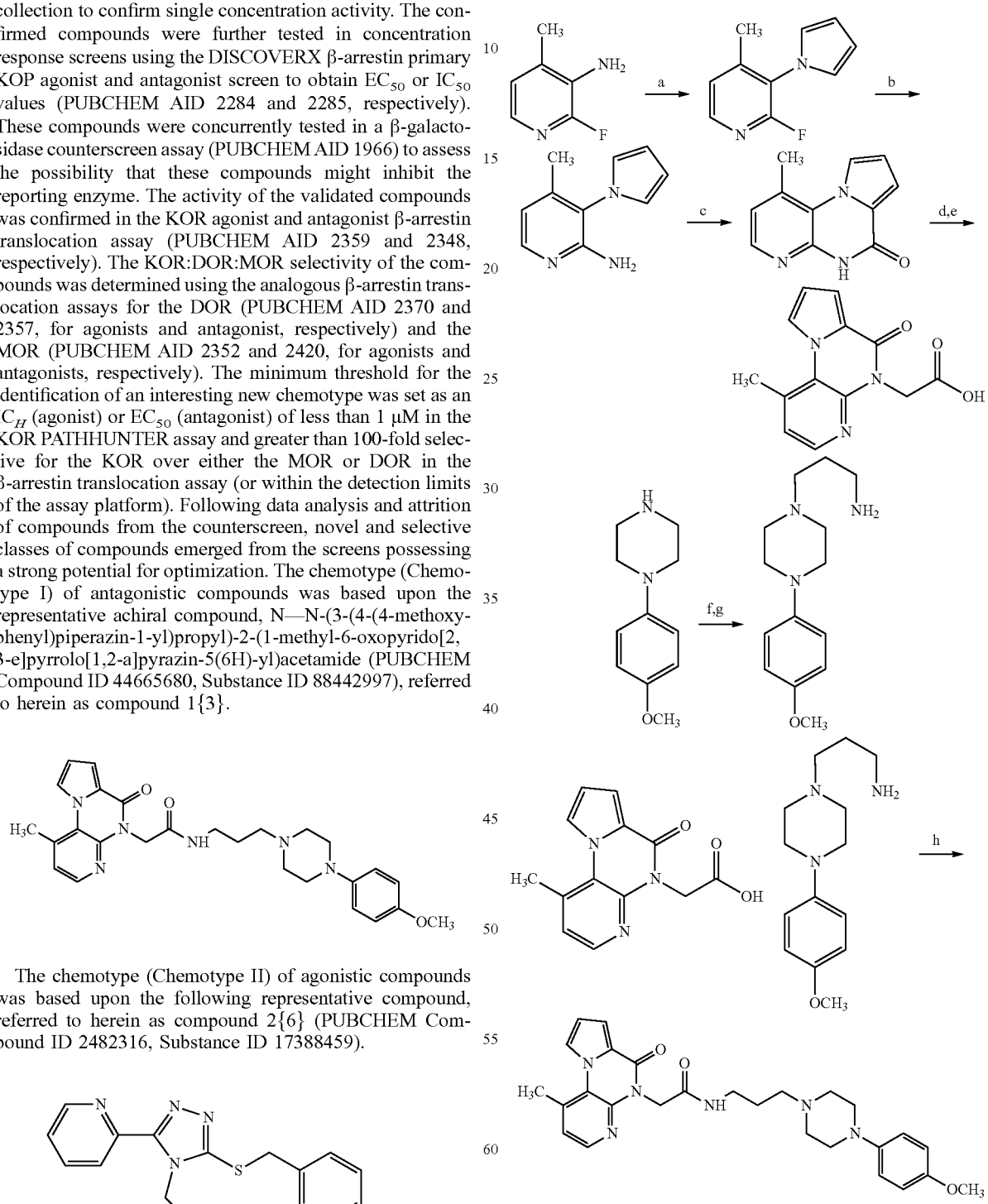

(a) 2, 5-dimethoxytetrahydrofuran, AcOH; (b) ammonia, MeOH, 150° C.; (c) triphosgene, toluene; (d) sodium hydride, methyl bromoacetate, DMF; (e) LiOH, MeOH:THF:H₂O; (f) acryl nitrile; (g) lithium aluminum hydride, ether; (h) DIC, DMAP, CH₂Cl₂.

2-Fluoro-4-methyl-3-(1H-pyrrol-1-yl)pyridine

1-Methylpyrido[2,3-e]pyrrolo[1,2-a]pyrazin-6(5H)-one

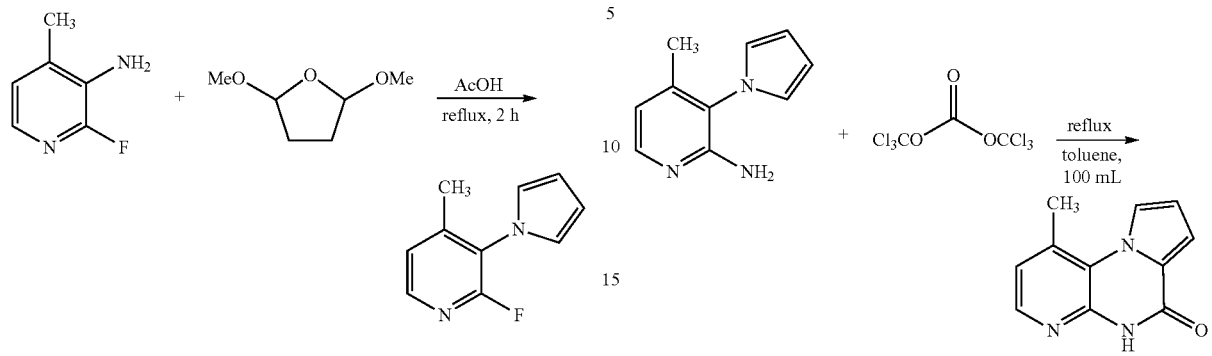

2-Fluoro-4-methylpyridin-3-amine (1.0 g, 7.93 mmol) and 2,5-dimethoxytetrahydrofuran (1.08 mL, 1.05 equiv.) were suspended in 3 mL of acetic acid and refluxed for 2 hours. The reaction was cooled down to room temperature. The solvents were removed and the residue was purified by silica gel chromatography (EtOAc/hexanes=1:8, Rf=0.3) to afford 1.0 g (72%) oil. $^1$H NMR (400 MHz, CDCl$_3$) δ 8.10 (dd, J=0.8, 5.1 Hz, 1H), 7.17 (d, J=5.1 Hz, 1H), 6.74 (td, J=2.1, 0.9 Hz, 2H), 6.40 (t, J=2.1 Hz, 2H), 2.26 (s, 3H). $^{13}$C NMR (101 MHz, CDCl$_3$) δ 160.2, 157.8, 149.6, 149.5, 145.5, 145.4, 123.80, 123.76, 122.1, 109.8, 17.29, 17.25. HRMS (m/z) calcd for C$_{10}$H$_{10}$FN$_2$ (M+H) 177.0828. found 177.0827. Richards, et al. (2008) *Bioorg. & Med. Chem. Lett.* 18:4325-27.

4-Methyl-3-(1H-pyrrol-1-yl)pyridine-2-amine (1.0 g, 5.8 mmol) and triphosgene (2.6 g, 8.7 mmol) were dissolved in 100 mL of toluene. The mixture was refluxed for 3 hours, then cooled to room temperature. The red solid was collected after filtration and washed with CH$_3$CN 0.5 g (43%). The material was used directly for the next step reaction without purification. $^1$H NMR (400 MHz, DMSO) δ 11.64 (s, 1H), 8.15 (dd, J=1.4, 2.9 Hz, 1H), 8.13 (d, J=4.9 Hz, 1H), 7.20-7.08 (m, 2H), 6.75 (dd, J=2.9, 3.9 Hz, 1H), 2.81 (s, 3H).

Methyl 2-(1-methyl-6-oxopyrido[2,3-e]pyrrolo[1,2-a]pyrazin-5(6H)-yl)acetate

4-Methyl-3-(1H-pyrrol-1-yl)pyridine-2-amine

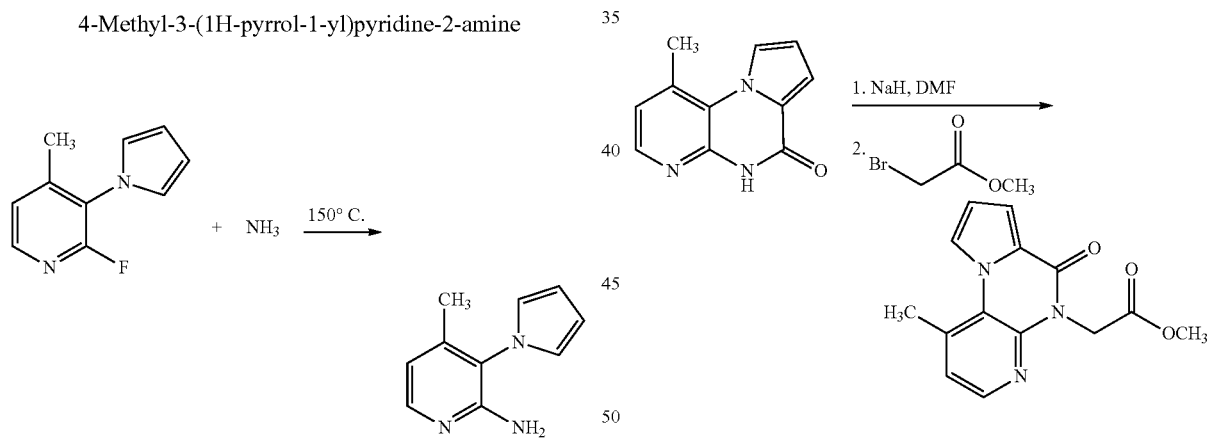

2-Fluoro-4-methyl-3-(1H-pyrrol-1-yl)pyridine (3.9 g, 22.1 mmol) was dissolved in 80 mL of ammonia solution (7N in MeOH) in a sealed tube (350 mL). The mixture was heated at 150° C. for 2 days protected with a blast shield. The mixture was cooled to room temperature, then cooled in the ice for minutes. The filtrate was evaporated to dryness and purified by flash chromatography (EtOAc/Hexanes=1:1, Rf=0.5) to give 2.9 g (76%) white solid. $^1$H NMR (400 MHz, CDCl$_3$) δ 7.96 (d, J=5.1 Hz, 1H) 6.67 (t, J=2.1 Hz, 2H), 6.60 (d, J=5.2 Hz, 1H), 6.41 (t, J=2.1 Hz, 2H), 4.52 (s, 2H), 2.02 (s, 3H). $^{13}$C NMR (101 MHz, CDCl$_3$) δ 156.1, 147.2, 145.9, 121.5, 121.1, 116.0, 110.0, 16.7. HRMS (m/z): calcd for C$_{10}$H$_{12}$N$_3$ (M+H) 174.1031. found 174.1026. Peet & Sunder (1986) *Heterocycles* 24:3213-3221.

To a solution of 1-methylpyrido[2,3-e]pyrrolo[1,2-a]pyrazin-6(5H)-one (50 mg, 0.25 mmol) in 2 mL of DMF, was added NaH (60%, 11 mg, 0.28 mmol). The mixture was stirred at room temperature for 1 hour. Methylbromoacetate (26 mL, 0.28 mmol) was added. The mixture was stirred for 16 hours. Solvents were removed under vacuum and the residue was purified by silica gel flash chromatography. (DCM/MeOH=1:10, Rf=0.5) to afford 37 mg (54%) light yellow solid. $^1$H NMR (400 MHz, CDCl$_3$) δ 8.15 (d, J=4.9 Hz, 1H), 7.95 (dd, J=1.5, 2.9 Hz, 1H) 7.36 (dd, J=1.5, 4.0 Hz, 1H), 7.00 (d, J=4.9 Hz, 1H), 6.71 (dd, J=2.9, 4.0 Hz, 1H), 5.25 (s, 2H), 3.77 (s, 3H), 2.83 (s, 3H). $^{13}$C NMR (101 MHz, CDCl$_3$) δ 169.3, 155.5, 143.1, 142.1, 134.8, 124.2, 122.7, 122.6, 120.4, 113.5, 113.4, 52.3, 41.9, 22.9. HRMS (m/z): calcd for C$_{14}$H$_{14}$N$_3$O$_3$ (M+H) 272.1035. found 272.1042.

2-(1-Methyl-6-oxopyrido[2,3-e]pyrrolo[1,2-a]pyrazin-5(6H)-yl)acetic acid

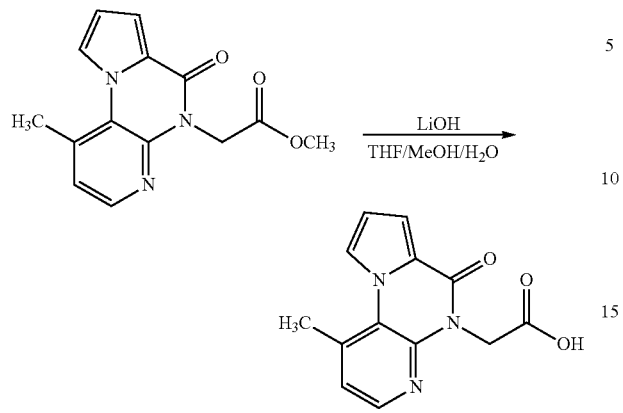

Methyl 2-(1-methyl-6-oxopyrido[2,3-e]pyrrolo[1,2-a]pyrazin-5(6H)-yl)acetate (517 mg, 1.91 mmol) was dissolved in 20 mL of MeOH/H$_2$O/THF (1:1:4). LiOH (68.5 mg, 2.86 mmol) was added. The mixture was stirred at room temperature for 16 hours. The solvents were removed and residue was dissolved in water, washed with ether, then neutralized with 2N HCl to pH=3. 356 mg (73%) white solid was obtained after filtration and dried under vacuum. $^1$H NMR (400 MHz, DMSO) δ 12.90 (s, 1H), 8.27-8.17 (m, 2H), 7.29-7.19 (m, 2H), 6.80 (dd, J=2.9, 3.9 Hz, 1H), 5.02 (s, 2H), 2.85 (s, 3H). $^{13}$C NMR (101 MHz, DMSO, APT) δ 169.8, 154.5, 143.1, 141.4, 135.9, 123.9, 123.3, 122.8, 119.5, 113.3, 112.7, 41.6, 22.2. HRMS (m/z): calcd for C$_{13}$H$_{12}$N$_3$O$_3$ (M+H) 258.0879. found 258.0894.

3-(4-(4-Methoxyphenyl)piperazin-1-yl)propanenitrile

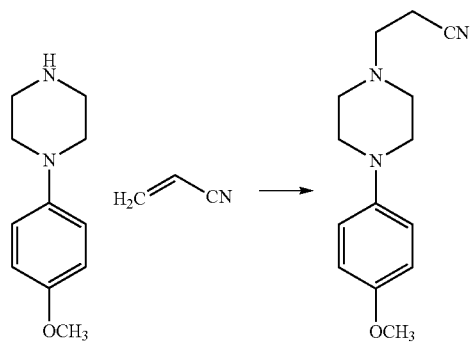

4-Methoxyphenylpiperazine (0.92 g, 4.68 mmol) and acrylonitrile (0.31 mL, 4.68 mmol) were mixed in a 10 mL reaction tube and stirred for 16 hours. The product was purified by silica gel flash chromatography (EtOAc/hexanes=1:8, Rf=0.3) to give 0.8 g (74%) white solid. $^1$H NMR (400 MHz, CDCl$_3$) δ 6.98-6.90 (m, 2H), 6.90-6.82 (m, 2H), 3.79 (s, 3H), 3.17-3.07 (m, 4H), 2.78 (t, J=7.0 Hz, 2H), 2.74-2.64 (m, 4H), 2.57 (t, J=7.0 Hz, 2H). $^{13}$C NMR (101 MHz, CDCl$_3$) δ 154.0, 145.5, 118.8, 118.4, 114.5, 55.6, 53.4, 52.8, 50.6, 15.9. Upadhayaya, et al. (2004) *Bioorg. Med. Chem.* 12:2225-2238.

3-(4-(4-Methoxyphenyl)piperazin-1-yl)propan-1-amine

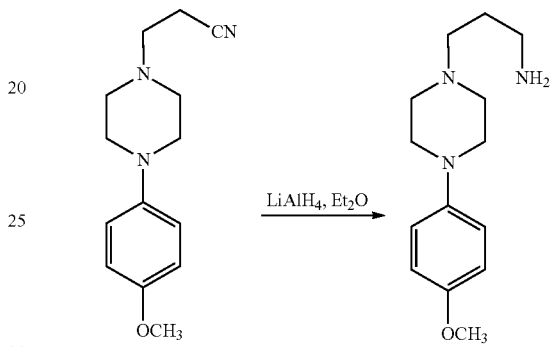

A solution of 3-(4-(4-methoxyphenyl) piperazin-1-yl)propanenitrile (0.8 g, 3.26 mmol) in 15 mL ether was added to the suspension of LiAlH$_4$ (0.19 g, 4.89 mmol) in 5 mL of ether. The mixture was stirred at room temperature for 16 hours, then quenched with 2N NaOH (1 mL). The ether phase was dried over MgSO$_4$ and evaporated to dryness to give 0.68 g (84%) white solid, which was used directly without further purification. $^1$H NMR (400 MHz, CDCl$_3$) δ 6.89 (d, J=9.1 Hz, 2H), 6.82 (d, J=9.1 Hz, 2H), 3.75 (s, 3H), 3.15-3.04 (m, 4H), 2.87 (s, br. 2H), 2.76 (t, J=6.8 Hz, 2H), 2.67-2.53 (m, 4H), 2.51-2.37 (m, 2H), 1.75-1.54 (m, 2H). $^{13}$C NMR (101 MHz, CDCl$_3$) δ 153.8, 145.7, 118.1, 114.4, 56.4, 55.5, 53.48, 50.6, 40.6, 30.1. Valenta, et al. (1990) *Collect. Czech. Chem. Commun.* 55:797-808.

N-(3-(4-(4-Methoxyphenyl)piperazin-1-yl)propyl)-2-(1-methyl-6-oxopyrido[2,3-e]pyrrolo[1,2-a]pyrazin-5(6H)-yl)acetamide

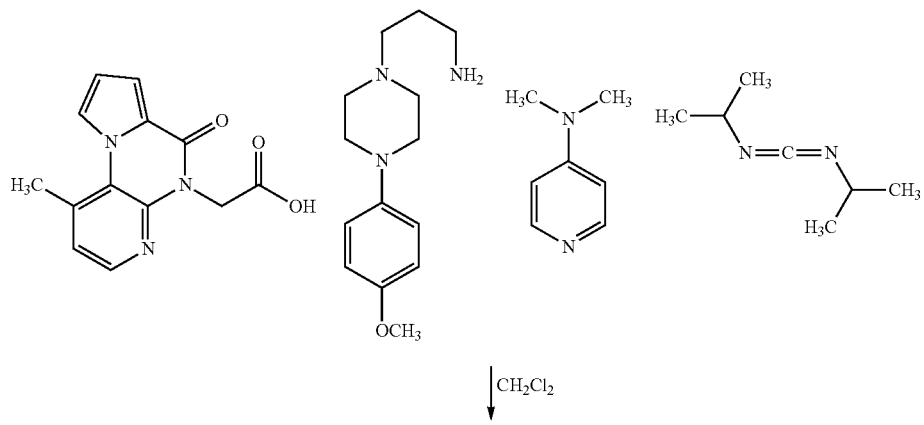

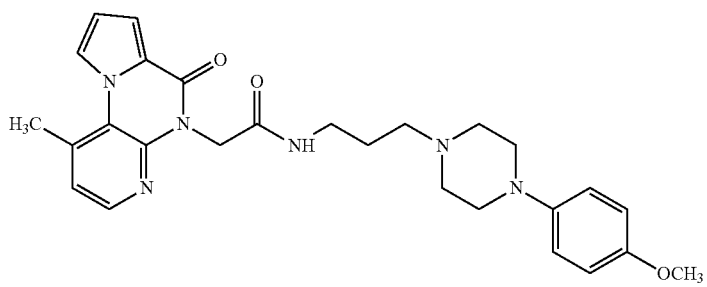

2-(1-Methyl-6-oxopyrido[2,3-e]pyrrolo[1,2-a]pyrazin-5(6H)-yl)acetic acid (30 mg, 0.12 mmol), 3-(4-(4-methoxyphenyl)piperazin-1-yl)propan-1-amine (43.6 mg, 0.17 mmol) and DMAP (1.4 mg, 0.012 mmol) were dissolved in 1 mL of DCM. Diisopropylcarbodiimide (0.09 mL, 0.58 mmol) was added. The mixture was stirred at room temperature for 16 hours and the product was purified by silica gel flash chromatography (DCM/MeOH=10:1, Rf=0.5) to give 30 mg (53%) white solid. $^1$H NMR (400 MHz, CDCl$_3$) δ 8.17 (d, J=4.9 Hz, 1H), 7.87 (dd, J=1.4, 2.9 Hz, 1H), 7.33 (dd, J=1.4, 4.0 Hz, 1H), 7.12 (s, 1H), 6.99 (d, J=5.0 Hz, 1H), 6.84 (s, 4H), 6.68 (dd, J=2.9, 4.0 Hz, 1H), 5.11 (s, 2H), 3.78 (s, 3H), 3.41 (dd, J=5.8, 12.0 Hz, 2H), 3.02-2.91 (m, 4H), 2.74 (s, 3H), 2.63-2.54 (m, 4H), 2.49 (t, J=6.4 Hz, 2H), 1.75-1.69 (m, 2H). $^{13}$C NMR (101 MHz, CDCl$_3$) δ 167.9, 155.8, 153.8, 145.4, 143.2, 142.3, 134.8, 124.1, 122.8, 122.6, 120.4, 118.0, 114.4, 113.5, 113.4, 57.3, 55.6, 53.4, 50.4, 44.2, 39.4, 25.2, 22.8. HRMS (m/z): calcd for C$_{27}$H$_{33}$N$_6$O$_3$ (M+H) 489.2609. found 489.2600.

Example 3

SAR Expansion and Optimization of Chemotype I

Synthetic chemistry was conducted for the new chemotype, and the analogues synthesized effectively represent a single round of optimization, therefore the decision of analogues synthesized was guided by the initial screening data and a limited set of commercially-available follow up compounds. Therefore, further optimization of the chemotype is contemplated. The short, flexible synthetic route of the instant scaffold allows easy preparation of additional analogs to hone in on the desired characteristics or allow the possible incorporation of mass detection or fluorescent markers. Both the malleability and optimization potential is illustrated through the following detailed account for the scaffold. A key feature of the instant chemotype is that it is a distinct, novel class of general KOR antagonists with sufficient analogues to demonstrate tractable SAR. The modular synthetic route to this class of compounds is summarized in Scheme 2.

SCHEME 2

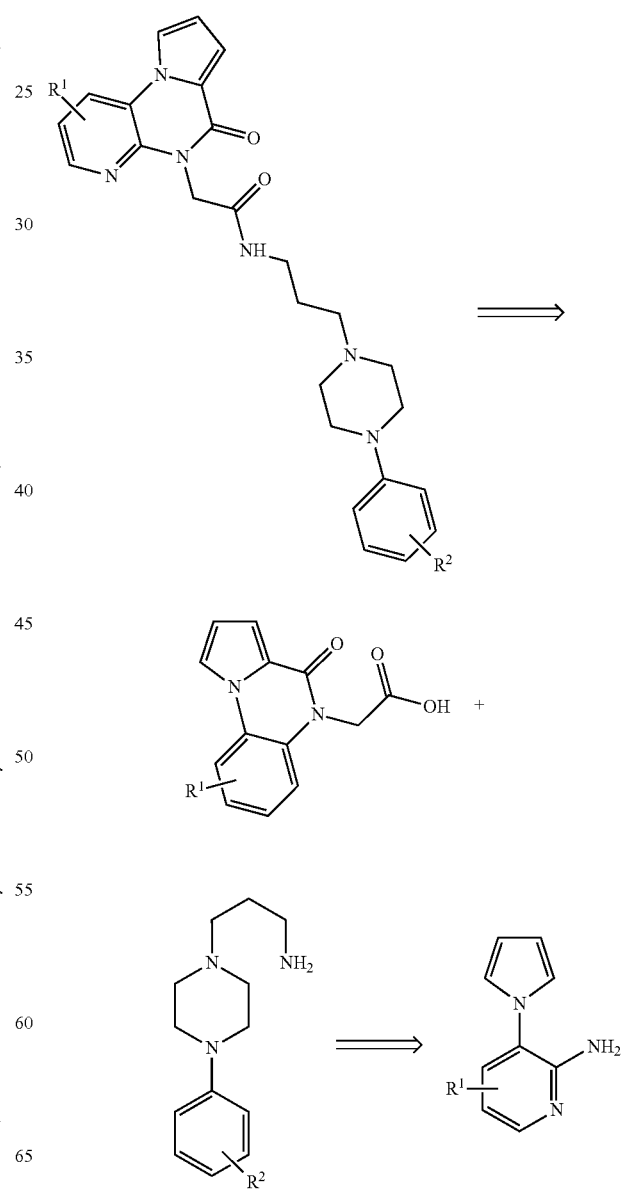

Example 4

Chemotype I Analogues

The HTS campaign for antagonists afforded the Chemotype I compounds with promising potency (compounds 1{1} and 1{2}, Table 1) as well as a number of analogues found to have $IC_{50}$ values above ten micromolar (Table 2). Notably, both compounds 1{1} and 1{2} contained a p-methoxyphenyl substituted piperazine moiety and a pyrrolopyrazinone core scaffold. An amide coupling-based synthetic route was developed to synthesize this chemotype, allowing the synthesis of 18 analogues in a single round of SAR. The synthetic efforts were augmented with the purchase of eight commercial analogues and a selection of the screening results is presented in Tables 1 and 2.

TABLE 2

| | | Potency (μM) Average ± S.E.M. (stdv/sqrt (n)) (n = replicates) | | | |
| | | Target | | Antitarget | |
| Entry 1{n} | n | KOR DRX | KOR HCS (n = 2) | MOR HCS (n = 2) | DOR HCS (n = 2) |
|---|---|---|---|---|---|
| 1 | 12 | 1.97 | 1.31 (n = 8) | >32 | >32 |
| 2 | | 4.32 | 15.3 | >32 | >32 |
| 3 | 8 | 0.12 | 0.003 (n = 4) | >32 | >32 |
| 4 | 8 | 0.19 | 0.004 (n = 6) | 30.9 | >32 |
| 5 | 8 | 0.43 | 0.045 (n = 4) | 17.2 | >32 |
| 6 | 8 | 0.69 | 0.07 | >32 | >32 |
| 7 | 4 | 0.88 | 2.28 | >32 | >32 |
| 8 | 4 | 4.95 | 2.56 | 22.5 | >32 |

TABLE 1

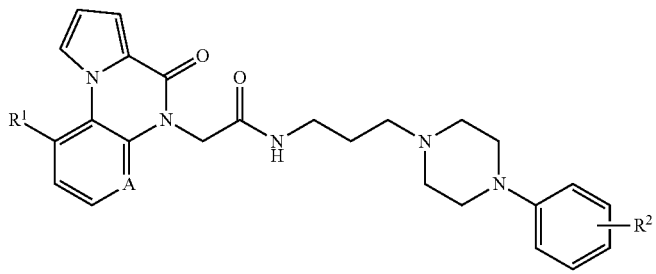

| Entry 1{n} | CID | SID | A | R¹ | R² |
|---|---|---|---|---|---|
| 1 | 22553442 | 87544476 87218790 90340552 | N | H | 4-OMe |
| 2 | 22522554 | 87218788 | C | H | 4-OMe |
| 3 | 44665680 | 88442997 | N | Me | 4-OMe |
| 4 | 44665679 | 88443000 | N | Me | 2,4-diOMe |
| 5 | 44665685 | 88442999 | N | Me | 3,4-OCH₂O |
| 6 | 44665687 | 88442998 | N | Me | 4-Cl |
| 7 | 44665686 | 88442996 | N | Me | 4-Me |
| 8 | 44665682 | 88442991 | N | Me | H |
| 9 | 44828478 | 90340555 | N | H | 2,4-diOMe |
| 10 | 44828479 | 90340554 | N | H | 3,4-OCH₂O |
| 11 | 44828476 | 90340553 | N | H | 4-Cl |
| 12 | 44828480 | 90340551 | N | H | 4-Me |
| 13 | 44828477 | 90340550 | N | H | H |

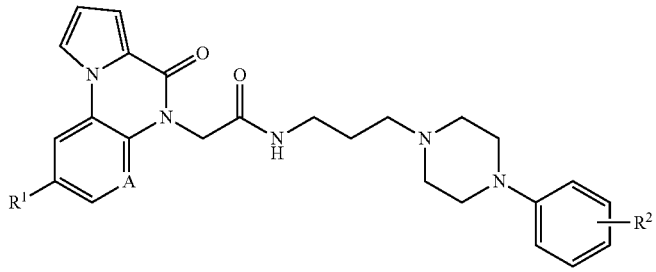

| Entry 1{n} | CID | SID | A | R¹ | R² |
|---|---|---|---|---|---|
| 14 | 45100475 | 92093149 | N | Br | 4-OMe |
| 15 | 45100474 | 92093150 | N | Br | 4-Cl |
| 16 | 45100477 | 92093151 | N | Br | 2,4-diOMe |
| 17 | 45100476 | 92093152 | N | Br | 3,4-OCH₂O |

CID, PUBCHEM Chemical ID; SID, PUBCHEM Substance ID.

TABLE 2-continued

| | | Potency (μM) Average ± S.E.M. (stdv/sqrt (n)) (n = replicates) | | | |
| | | Target | | Antitarget | |
| Entry 1{n} | n | KOR DRX | KOR HCS (n = 2) | MOR HCS (n = 2) | DOR HCS (n = 2) |
|---|---|---|---|---|---|
| 9 | 4 | 2.65 | 0.49 | 10.8 | >32 |
| 10 | 4 | 4.23 | 0.78 | >32 | >32 |
| 11 | 8 | 5.18 | 0.096 | >32 | >32 |
| 12 | 4 | 3.68 | 0.89 (n = 4) | 18.8 (n = 4) | >32 |
| 13 | 2 | >20 | 12.7 (n = 4) | >32 | >32 |
| 14 | 4 | 3.05 | 0.69 | 10.3 | >32 |
| 15 | 4 | >20 | >32 | 5.32 | >32 |
| 16 | 4 | 2.82 | 3.02 | 10.22 | >32 |
| 17 | 8 | 3.11 | 0.15 | >32 | >32 | n value in column refers to KOR DRX replicates.

Unexpectedly, the incorporation of a single methyl group on the heterocyclic core increased the potency of the p-methoxyphenyl substituted piperazine analogue by over ten fold in the β-arrestin assay and afforded the KOR-selective compound 1{3} with a high content β-arrestin translocation assay $IC_{50}$ of 3 nM. While less potent than JDTic ($IC_{50}$=0.02 nM), this compound was over 10,000-fold selective for the KOR over both the DOR and MOR, an improved selectivity compared to JDTic (202-fold selective for the KOR over the MOR). Based on these merits, compound 1{3} was nominated as an MLPCN probe compound. Several other compounds sharing the additional methyl group also exceeded the probe criteria to a lesser extent (Table 2, compound 1{4} through 1{7}). For several compounds, a slight loss in selectivity against the MOR counterscreen was observed (compounds 1{4}, 1{5}, 1{8}, 1{9}, 1{12}, 1{14} and 1{16}). This trend was amplified for compound 1{16}, which was a MOR-selective antagonist of modest potency (5.32 μM). The present probe candidate could be utilized for additional studies in this area or further refined through additional rounds of SAR to optimize this disparity, further increase potency or improve other desirable characteristics. This scaffold is highly amenable to modification via the present synthetic route and various substituents of this chemotype are contemplated.

Moreover SAR analysis of the phenylpiperazine moiety was conducted (Table 3). It was observed that these analogues conferred a drastic loss in activity (Table 4). The compounds in entries 1{26} (CID 45479166) and 1{27} (CID 45479168) demonstrated the connection between tether length and activity, wherein the lower activity of both the two carbon and four carbon tether analogues indicates that the three-carbon tether length is optimal. It was noted that entries 1{24} (CID 22553452) and 1{25} (CID 22553453) could provide lead structures for a MOP receptor-selective compound based on the present scaffold.

TABLE 3

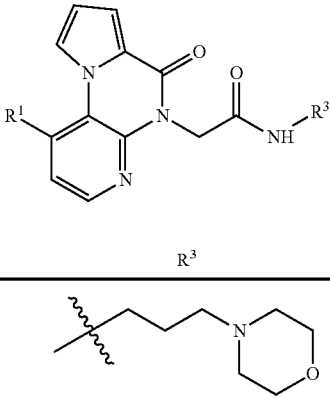

| Entry 1{n} | CID | SID | R¹ | R³ |
|---|---|---|---|---|
| 19 | 22553408 | 87544473 | H | 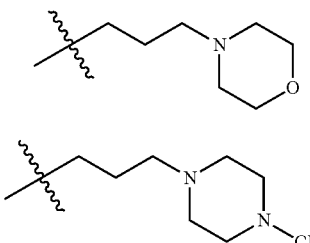 |
| 20 | 22553432 | 87544474 | H | 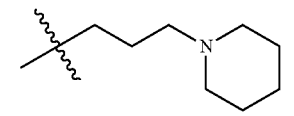 [SMILES: *CCCN1CCCCC1] |
| 21 | 22553433 | 87544475 | H | 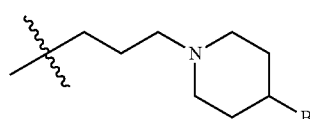 |
| 22 | 22553447 | 87544477 | H | 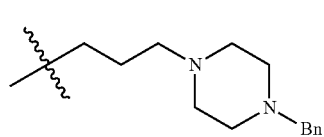 [SMILES: *CCCN1CCN(Cc2ccccc2)CC1] |
| 23 | 22553448 | 87544478 | H | |

TABLE 3-continued

| Entry 1{n} | CID | SID | R¹ | R³ |
|---|---|---|---|---|
| 24 | 22553452 | 87544479 | H | butyl-piperazine-(2-methyl-5-chlorophenyl) |
| 25 | 22553453 | 87544480 | H | propyl-piperazine-(2,3-dimethylphenyl) |
| 26 | 45479166 | 93575685 | Me | propyl-piperazine-(4-methoxyphenyl) |
| 27 | 45479168 | 93575686 | Me | pentyl-piperazine-(4-methoxyphenyl) |

CID, PUBCHEM Chemical ID; SID, PUBCHEM Substance ID.

TABLE 4

| | | Potency (μM) Average ± S.E.M. (stdv/sqrt (n)) (n = replicates) | | | |
|---|---|---|---|---|---|
| | | Target | | Antitarget | |
| Entry 1{n} | n | KOR DRX | KOR HCS (n = 2) | MOR HCS (n = 2) | DOR HCS (n = 2) |
| 19 | 4 | >20 | >32 | >32 | >32 |
| 20 | 4 | >20 | >32 | >32 | >32 |
| 21 | 4 | >20 | >32 | >32 | >32 |
| 22 | 4 | 4.78 | 1.31 | >32 | >32 |
| 23 | 4 | >20 | 21.5 | >32 | >32 |
| 24 | 4 | >20 | >32 | 3.98 | >32 |
| 25 | 4 | >20 | >32 | 6.33 | >32 |
| 26 | 4 | 14.1 | >32 | >32 | >32 |
| 27 | 8 | 1.25 | 0.005 (n = 4) | >32 | >32 | n value in column refers to KOR DRX replicates.

Example 5

Pharmacology and ADMET Properties of Declared Antagonist Probe Compound

The broader selectivity of compound 1{3} was tested against additional targets and basic pharmacological properties were assessed. Compound 1{3} was subjected to a binding assay panel of 44 GPCR and other molecular targets utilizing the resources of the Psychoactive Drug Screening Program (PDSP) (Table 5). The compound was initially screened in radioligand binding assays at a constant concentration (10 μM) to identify possible activity of the compound. Results showing significant activity in the initial screen were selected for $K_i$ determinations.

TABLE 5

| GCPR | $K_i$ (nM) | GCPR | $K_i$ (nM) |
|---|---|---|---|
| 5ht1a | X | D2 | 1,346 |
| 5ht1b | X | D3 | 250 |
| 5ht1d | 702 | D4 | X |
| 5ht1e | X | D5 | X |
| 5ht2a | X | DAT | * |
| 5ht2b | 1,922 | DOR | 1,443 |
| 5ht2c | X | GabaA | X |
| 5ht3 | X | H1 | 454 |
| 5ht5a | X | H2 | 3,502 |
| 5ht6 | X | H3 | X |
| 5ht7 | X | H4 | X |
| Alpha1A | X | KOR | 129 |
| Alpha1B | X | M1 | X |
| Alpha1D | X | M2 | X |
| Alpha2A | X | M3 | X |
| Alpha2B | 7,695 | M4 | X |
| Alpha2C | 694 | M5 | 6,397 |
| Beta1 | X | MOR | 1,585 |
| Beta2 | X | NET | 685 |
| Beta3 | X | SERT | 5,326 |
| BZP Rat Brain Site | X | Sigma1 | X |
| D1 | X | Sigma2 | X |

X, $K_i$ >10,000 or missed in primary screen.
* Assay results pending.

Overall, the Chemotype I probe 101 displayed a slightly cleaner binding profile than other antagonist compounds tested (compounds of a different chemotype), although this probe did possess a rather high affinity for the D3 receptor ($K_i$=250 nM). This affinity, while not optimal, may also encourage its development as a D3 receptor antagonist. Compounds of this type have also shown great promise in the treatment of addictive disorders (Heidbreder & Newman (2010) *Ann. N. Y. Acad. Sci.* 1187:4-34). The KOR binding affinity ($K_i$=129 nM) was in excellent agreement with the 120 nM (DISCOVERX) estimate for the $IC_{50}$ inhibition of KOR response to dynorphin A.

In addition to profiling the selectivity of this class of KOR ligands, basic pharmacological properties were assessed. Thus, compound 1{3} of Chemotype I was characterized by a variety of screens including aqueous solubility, PAMPA (Parallel Artificial Membrane Permeability Assay), plasma protein binding, plasma stability, and hepatic microsome stability.

The results of this analysis indicated that compound 1{3} had a reasonable solubility of 12.9 μg/mL in 137 mM NaCl, 2.7 mM KCl, 10 mM sodium phosphate dibasic, 2 mM potassium phosphate monobasic, pH 7.4 (PBS) at room temperature (23° C.). At acidic pHs, the solubility of the compound improved dramatically to >90 ug/mL (96.6 μg/ml at pH 5.0 and 90.6 μg/ml at pH 6.2). In addition, this compound possessed superior stability at room temperature in PBS in the absence of any antioxidants or other protectants (<0.1% DMSO v/v) with 94.42% of the parent compound remaining after 48 hours of incubation.

PAMPA is used as an in vitro model of passive, transcellular permeability. An artificial membrane immobilized on a filter is placed between a donor and acceptor compartment. At the start of the test, drug is introduced in the donor compartment (at various pH). Following the permeation period, the concentrations of compound in the donor compartment and acceptor compartment are measured using UV spectroscopy. In this assay, compound 1{3} had a moderate permeability of $27 \times 10^{-6}$ cm/s at pH 5 that increased to $227 \times 10^{-6}$ cm/s at pH 6.2 and to $757 \times 10^{-6}$ cm/s as the pH rose to 7.4, consistent with loss of protonation and positive charge, which would improve permeability. This probe exhibited moderate permeability in the blood brain barrier PAMPA assay (donor and acceptor compartments both at pH 7.4) of $51 \times 10^{-6}$ cm/s.

Plasma protein binding is a measure of a drug's efficiency to bind to the proteins within blood plasma. The less bound a drug is, the more efficiently it can traverse cell membranes or diffuse. Highly plasma protein bound rugs are confined to the vascular space, thereby having a relatively low volume of distribution. In contrast, drugs that remain largely unbound in plasma are generally available for distribution to other organs and tissues. In the instant case, the Chemotype I antagonist 1{3} was marginally available with 88.46% and 80.07% bound to 1 μM and 10 μM mouse plasma protein, respectively, and 93.96% and 88.54% bound to 1 μM and 10 μM human plasma protein, respectively.

Plasma stability is a measure of the stability of small molecules and peptides in plasma and is an important parameter that can strongly influence the in vivo efficacy of a test compound. Drug candidates are exposed in plasma to enzymatic processes (proteinases, esterases), and they can undergo intramolecular rearrangement or bind irreversibly (covalently) to proteins. Compound 1{3} showed excellent stability (100% remaining after 3 hours) in both human and mouse plasma.

The microsomal stability assay is commonly used to rank compounds according to their metabolic stability. This assay addresses the pharmacologic question of how long the parent compound will remain circulating in plasma within the body. Compound 1{3} was found to be long lasting with 22% and 7.3% (for human and mouse microsomes, respectively) remaining after 1 hour.

Compound 1{3} was also screened against the NCI-60 panel of human tumor cell lines. The compound was screened against each cell line in a single dose at 10 μM. No significant inhibition of tumor cell growth was observed. The absence of selective cytotoxicity was expected given that the compound was developed to target the KOR.

Three of the most potent and selective of the KOR antagonists, NorBNI, GNTI, and JDTic have been recognized for their long acting properties at the KOR that may be associated with JNK activation. While they have common structural features their differences are sufficient to cloud the SAR that underlies this long acting physiological behavior that can be blocked by reversible nonselective opioid antagonists. It is therefore important to determine how this selective, structurally novel chemotype functions at the KOR with respect to NorBNI, GNTI, and JDTic. Of particular interest is whether the probe is long or short acting at the KOR, and studies of this question in cells and animal models may clarify as to whether the underlying mechanism for antagonist anti-addictive behavior requires activation of JNK.

Example 6

Mechanism of Action Analysis of Chemotype I

To determine where in the pathway for GPCR activation of the KOP receptor compound 1{3} acted, mechanism of action studies were carried out. Compound 1{3} and the isosteric analog compound 1{1}, lacking the 4-methyl substitution and the nitrogen heteroatom of the pyridine group, were compared, with Nor-BNI as a control. As evidenced by the data presented in Table 6, compound 1{3} was found to be a potent inhibitor of the $^{35}$S-GTPγS coupling, indicating a direct functional effect on G-coupling. Potency was comparable to the β-arrestin translocation HCS assay.

TABLE 6

| Ligand | IC$_{50}$, nM | Imax (% NBNI) |
|---|---|---|
| Nor-BNI | 4.64 ± 0.83 | 101 ± 1 |
| Compound 1{1} | 95.7 ± 48 | 122 ± 5[a] |
| Compound 1{3} | 434.2 ± 154.1[a] | 117 ± 5[a] | n ≥ 3 curves performed in duplicate.

Ligand vs. NBNI: [a]$p < 0.05$; t-test n ≥ 3.

In addition, compound 1{3} was observed to be a potent inhibitor of the downstream ERK 1/2 activation pathway (Table 7), the potency of which was comparable to the β-arrestin translocation HCS assay.

TABLE 7

| Ligand | IC$_{50}$, nM | Imax (% NBNI) |
|---|---|---|
| Nor-BNI | 4.46 ± 0.64 | 100 ± 0.3 |
| Compound 1{1} | 65 ± 9.2[a] | 101 ± 3 |
| Compound 1{3} | 330.0 ± 29.4[a,b] | 90 ± 2[a] | n ≥ 3 curves performed in replicates of 6.
Ligand vs. NBNI: [a]$p < 0.001$;
Ligand vs. Compound 1{3}: [b]$p < 0.001$, t-test.

Interestingly, it appeared that when KOR β-arrestin potencies were enhanced, the G protein coupling and ERK activation potencies were diminished. This could be an example of functional selectivity.

Example 7

SAR Expansion and Optimization of Chemotype II

Optimization of Chemotype II compound was also carried out. The modular synthetic routes to this class of compounds, summarized in Scheme 3, permitted the rapid exploration of structure-activity relationships. This Chemotype could be readily assembled from commercially-available or easily-accessed fragments, thus allowing the introduction of new functional groups or core modifications.

SCHEME 3

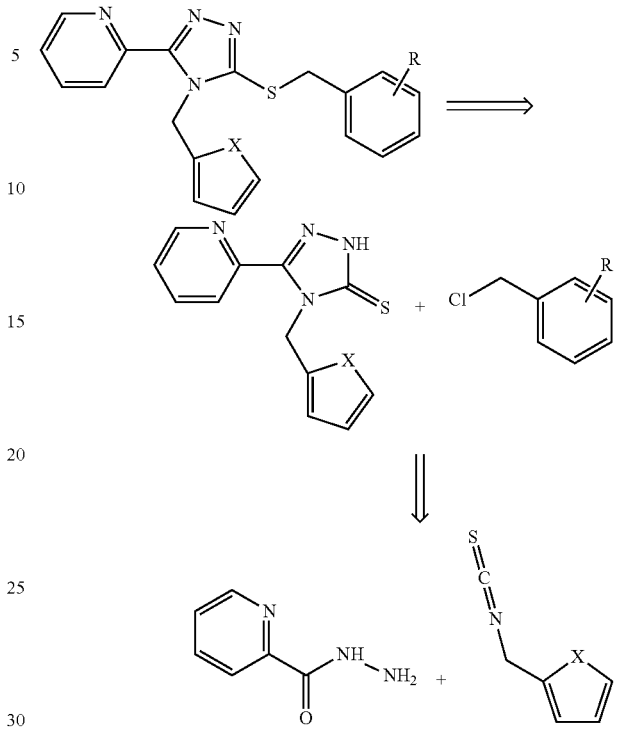

The HTS screening campaign for the triazole-based Chemotype II originally uncovered four compounds with potencies around 2 μM and one example at 6.7 μM (Tables 8 and 9, entries 1 and 3-6). While a number of Chemotype II analogues were commercially available, limited substitution on the phenyl ring and no available thiophene-containing analogues led to the adoption of an entirely synthetic approach based on precedented chemistry. Beginning with the appropriate isothiocyanate and 2-picolynyl hydrazide, the 1,2,4-triazole-3-thione scaffolds were synthesized in two steps with excellent yields (77-82% overall yields) without chromatographic separations (Burbuliene, et al. (2009) ARKIVOC 281-289).

By way of illustration, compound 2{9} was synthesized as follows.

N-(Thiophen-2-ylmethyl)-2-picolinoylhydrazine carbothioamide

2-Picolynyl hydrazide (883 mg, 6.44 mmol) and thiophene isothiocyanate (1,000 mg, 6.44 mmol) in MeCN (20 mL) were stirred for 16 hours at room temperature. The reaction mixture was filtered, the precipitate washed with additional MeCN (3×10 mL) and dried under vacuum to afford the thioamide as an off-white solid (1,642 mg, 5.62 mmol, 87% yield), which was used without further purification. Mp 175-178° C.; $^1$H NMR (DMSO-d6) δ 4.84 (d, J'=6.0 Hz, 2H), 6.93 (m, 1H), 7.00 (m, 1H), 7.36 (dd, J=1.2, 4.8 Hz, 1H), 7.63 (m, 1H), 8.03 (m, 2H), 8.56 (br s, 1H), 8.66 (d, J=4.8 Hz, 1H), 9.50 (br s, 1H), 10.60 (s, 1H); $^{13}$C NMR (DMSO-d6) δ d 122.5, 124.9, 125.8, 126.2, 126.9, 137.6, 148.4; u 42.1, 141.9, 149.3, 181.4, 198.3; IR (neat) 3141, 1672, 1527, 1499, 1466 cm$^{-1}$; HRMS (ESI) m/z calcd for $C_{12}H_{13}N_4OS_2$ ([M+H]$^+$), 293.0531. found 293.0516.

4-(Thiophene-2-ylmethyl)-3-(pyridin-2-yl)-1H-1,2,4-triazole-5(4H)-thione

To a slurry of the above thioamide (602 mg, 2.06 mmol) in water (25 mL) was added NaOH (4.00 g, 100 mmol). The reaction was heated at reflux for 2 hours; the starting thioamide dissolving promptly upon warming. The reaction was cooled to room temperature, diluted with aqueous HCl (1 N, 20 mL) and acidified to pH=6 with concentrated HCl. The solid precipitate was filtered, washed with water (2×15 mL) and dried under vacuum to afford the thiophene thione as a white solid (530 mg, 1.93 mmol, 94% yield), which was used without further purification. Mp 229-231° C.; $^1$H NMR (DMSO-d6) δ 6.02 (s, 2H), 6.87 (dd, J=3.2, 4.8 Hz, 1H), 7.09 (d, J=2.4 Hz, 1H), 7.34 (dd, J=0.8, 5.2 Hz, 1H), 7.59 (q, J=4.4 Hz, 1H), 7.99 (d, J=4.4 Hz, 2H), 8.80 (d, J=4.8 Hz, 1H), 14.2 (br s, 1H), 10.60 (s, 1H); $^{13}$C NMR (DMSO-d6) δ d 122.8, 125.5, 126.3, 126.5, 128.1, 138.0, 149.0; u 42.3, 137.8, 145.5, 147.8, 168.3; IR (neat) 3019, 2896, 1584, 1549, 1501, 1462 cm$^{-1}$; HRMS (ESI) m/z calcd for $C_{12}H_{11}N_4S_2$ ([M+H]$^+$), 275.0475. found 275.0412.

2-(5-((3,4-Dichlorobenzyl)thio)-4-(thiophen-2-ylmethyl)-4H-1,2,4-triazol-3-yl)pyridine 2{9}

The thiophene thione (65 mg, 0.24 mmol), $K_2CO_3$ (66 mg, 0.48 mmol) and 2,4-dichlorobenzyl chloride (56 mg, 0.28 mmol) were combined in acetone (3 mL) and stirred in a sealed vial for 15 hours. The solvent was removed and the residue washed with $CH_2Cl_2$ (2×3 mL) then filtered. The combined filtrates were concentrated and purified by silica chromatography to afford the triazole product as an off-white solid (92 mg, 0.21 mmol, 90% yield). Mp 162-163° C.; $R_f$=0.24 (1:1 hexanes: EtOAc); $^1$H NMR (CDCl$_3$) δ 4.42 (s, 2H), 5.93 (s, 2H), 6.85 (dd, J=3.6, 4.8 Hz, 1H), 6.98 (d, J=2.4 Hz, 1H), 7.15 (dd, J=0.8, 4.8 Hz, 1H), 7.23 (dd, J=1.6, 8.0 Hz, 1H), 7.33 (m, 2H), 7.48 (d, J=2.0 Hz, 1H), 7.80 (dt, J=1.6, 8.0 Hz, 1H), 8.29 (d, J=8.0 Hz, 1H), 8.66 (d, J=3.6 Hz, 1H); $^{13}$C NMR (CDCl$_3$) δ d 123.2, 124.3, 126.4, 126.5, 127.7, 128.6, 130.6, 131.0, 137.1, 148.6; u 36.6, 43.8, 131.9, 132.6, 137.7, 147.6 (×2), 152.0, 152.5; IR (neat) 3052, 1589, 1568, 1463 cm$^{-1}$; HRMS (ESI) m/z calcd for $C_{19}H_{15}Cl_2N_4S_2$ ([M+H]$^+$), 433.0115. found 433.0108.

The subsequent coupling with a wide range of benzyl halides proceeded smoothly in acetone facilitated by $K_2CO_3$ (Dilanyan, et al. (2008) *Chem. Heterocycl. Compd.* 44:1395-1397) to readily furnish over 75 compounds, a selection of which is shown in Table 8.

TABLE 8

| Entry 2{n} | CID | SID | X | R | Purity (%) | Yield (%) |
|---|---|---|---|---|---|---|
| 1 | 662944 | 87218751 | O | 2,4-dichloro | ND | NA |
| 2 | 44601469 | 87334048 | S | 2,4-dichloro | >99 | 76 |
| 3 | 663290 | 87218759 | O | 4-bromo | ND | NA |
| 4 | 44601472 | 87334045 | S | 4-bromo | >99 | 53 |
| 5 | 1982054 | 4260946 | O | Styryl$^a$ | ND | NA |
| 6 | 2482316 | 17388459 | O | 4-t-butyl | ND | NA |
| 7 | 662263 | 860989 | O | 3-chloro | ND | NA |
| 8 | 44601470 | 87334039 | O | 3,4-dichloro | >99 | 77 |
| 9 | 44601475 | 87334049 | S | 3,4-dichloro | >99 | 90 |
| 10 | 44620914 | 87544155 | O | 4-chloro-3-trifluoromethyl | 98 | 68 |
| 11 | 44620925 | 87544171 | S | 4-chloro-3-trifluoromethyl | 99 | 86 |
| 12 | 44601474 | 87334041 | O | 4-methyl | >99 | 65 |
| 13 | 44601473 | 87334044 | S | 4-methyl | >99 | 88 |
| 14 | 44620937 | 87544143 | O | 4-trifluoromethyl | >99 | 57 |
| 15 | 44620933 | 87544159 | S | 4-trifluoromethyl | 99 | 93 |
| 16 | 44620923 | 87544150 | O | 3,5-difluoro | 97 | 83 |
| 17 | 44620926 | 87544166 | S | 3,5-difluoro | 99 | 66 |
| 18 | 44620927 | 87544153 | O | 2,4,6-trimethyl | 99 | 80 |
| 19 | 44620916 | 87544169 | S | 2,4,6-trimethyl | 99 | 43 |
| 20 | 2562032 | 87334040 | O | 4-methoxy | >99 | 97 |
| 21 | 44601471 | 87334046 | S | 4-methoxy | >99 | 88 |
| 22 | 44601466 | 87334042 | O | H | >99 | 70 |
| 23 | 46601467 | 87334043 | S | H | >99 | 83 |
| 24 | 44601468 | 87334047 | S | 2,4-difluoro | 93 | 72 |
| 25 | 1423675 | 87544141 | O | 4-nitro | >99 | 48 |
| 26 | 44620924 | 87544157 | S | 4-nitro | 93 | 60 |
| 27 | 44620930 | 87544142 | O | 4-cyano | 97 | 74 |
| 28 | 44620938 | 87544158 | S | 4-cyano | 99 | 88 |
| 29 | 44620928 | 87544144 | O | 4-methylcarboxylate | >99 | 60 |
| 30 | 44620922 | 87544160 | S | 4-methylcarboxylate | 99 | 83 |
| 31 | 4462915 | 87544145 | O | 4-acetoxy | 94 | 41 |
| 32 | 44620931 | 87544149 | S | 4-acetoxy | 98 | 55 |
| 33 | 44620920 | 87544146 | O | 4-isopropyl | >99 | 62 |

TABLE 8-continued

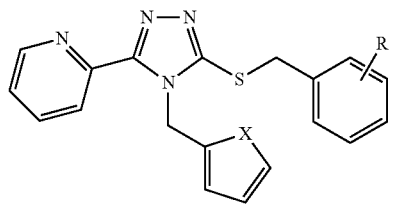

| Entry 2{n} | CID | SID | X | R | Purity (%) | Yield (%) |
|---|---|---|---|---|---|---|
| 34 | 44620929 | 87544162 | S | 4-isopropyl | 99 | 78 |
| 35 | 16447357 | 87544147 | O | 2-methyl | 99 | 57 |
| 36 | 44620912 | 87544163 | S | 2-methyl | 99 | 64 |
| 37 | 44620913 | 87544148 | O | 3-methoxy | 98 | 88 |
| 38 | 44620918 | 87544164 | S | 3-methoxy | 99 | 67 |
| 39 | 44620932 | 87544149 | O | 2-methyl-3-nitro | 95 | 97 |
| 40 | 44620917 | 87544165 | S | 2-methyl-3-nitro | >99 | 81 |
| 41 | 16447354 | 87544151 | O | 2,6-difluoro | 99 | 73 |
| 42 | 44620936 | 87544167 | S | 2,6-difluoro | 98 | 98 |
| 43 | 44620919 | 87544152 | O | 2,3,4-trifluoro | 99 | 88 |
| 44 | 44620921 | 87544168 | S | 2,3,4-trifluoro | >99 | 80 |
| 45 | 44620935 | 87544154 | O | 4-fluoro-2-trifluoromethyl | 99 | 74 |
| 46 | 44620911 | 87544170 | S | 4-fluoro-2-trifluoromethyl | 99 | 43 |
| 47 | 662723 | 87544156 | O | 2-chloro | >99 | 79 |
| 48 | 44620934 | 87544172 | S | 2-chloro | 99 | 76 |

[a]Styryl side chain in place of the substituted benzyl group.

Mindful of classical SAR substitution strategies (Topliss (1977) *J. Med. Chem.* 20:463-469; Hajduk & Sauer (2008) *J. Med. Chem.* 51:553-564), the instant approach was to vary the substitution on the phenyl ring, which produced two submicromolar analogues (entries 8 to 11, Table 9). Interestingly, some compounds containing substituted phenyl rings displayed >100% $E_{max}$ values at the highest concentration tested (as compared to dynorphin A ($E_{max}$=100%)).

TABLE 9

| Entry 2{n} | $E_{max}$ (%) | Average Potency (µM) | | | $K_i$ (nM) |
|---|---|---|---|---|---|
| | | KOR DRx[a] | KOR HCS[b] | MOR HCS[b] | |
| 1 | ~100 | 1.86 ± 0.07 | 0.93 | >32 | |
| 2 | ~120 | 2.27 ± 0.46 | 8.11 | >32 | |
| 3 | ~100 | 1.92 ± 0.05 | 1.36 | >32 | |
| 4 | ~185 | 1.85 ± 0.11 | 1.10 | >32 | |
| 5 | ~100 | 2.22 ± 0.10 | 1.43 | >32 | |
| 6 | ~100 | 2.01 ± 0.07 | 0.60 | >32 | |
| 7 | ~100 | 6.76 ± 0.01 | 3.63 | >32 | |
| 8 | ~140 | 0.87 ± 0.06 | 0.347 | >32 | 2 |
| 9 | ~135 | 0.73 ± 0.11 | 0.43 | >32 | |
| 10 | ~122 | 0.50 | 0.46 | >32 | |
| 11 | ~109 | 0.43 | 1.4 | >32 | 3 |
| 12 | ~150 | 6.20 ± 1.26 | 5.21 | >32 | 16 |
| 13 | ~170 | 3.59 ± 0.30 | 2.38 | >32 | |
| 14 | ~166 | 2.77 | 1.25 | >32 | |
| 15 | ~149 | 1.23 | 0.6 | >32 | |
| 16 | ~104 | 7.89 | 21.0 | >32 | |
| 17 | ~150 | 7.20 | >17.8 | >32 | 94 |
| 18 | ~100 | 15.0 | 9.8 | >32 | |
| 19 | ND | >20 | 9.5 | >32 | |
| 20 | ~150 | 7.70 ± 1.47 | 12.4 | >32 | 28 |
| 21 | ~130 | 9.62 ± 1.32 | 5.98 | >32 | 7.1 |
| 22 | $E_{max}$ not reached | >17.90 | >32 | >32 | 155 |
| 23 | ~150 | 13.85 ± 1.18 | 23.5 | >32 | 138 |
| 24 | ~155 | 6.74 ± 0.97 | 5.68 | >32 | |
| 25 | ~120 | 2.48 | 2.35 | >32 | |
| 26 | ~128 | 1.24 | 0.96 | >32 | |
| 27 | ~105 | 6.79 | 19.0 | >32 | |
| 28 | ~142 | 4.64 | 3.5 | >32 | |
| 29 | ~125 | 6.62 | 18.5 | >32 | |
| 30 | ~154 | 6.14 | 6.0 | >32 | |
| 31 | ND | >20 | >32 | >32 | |
| 32 | ND | >20 | >32 | >32 | |
| 33 | 165 | 5.97 | 2.8 | >32 | |
| 34 | ~100 | 3.66 | 2.2 | >32 | 2.3 |
| 35 | ND | >18.8 | >30 | >32 | 123 |
| 36 | ND | >16.0 | 14.5 | >32 | 68 |
| 37 | ND | >17.6 | >32 | >32 | 67 |
| 38 | ~100 | 8.72 | 12.2 | >32 | |
| 39 | ~128 | 8.21 | 12.0 | >32 | |
| 40 | ~105 | 5.81 | 4.2 | >32 | |
| 41 | ND | >20 | >32 | >32 | 55 |
| 42 | ND | >19.0 | 20.9 | >32 | 78 |
| 43 | ~140 | 7.00 | 5.3 | >32 | |
| 44 | ~115 | 3.04 | 1.7 | >32 | |
| 45 | ~138 | 8.27 | 5.4 | >32 | |
| 46 | ~109 | 4.46 | 2.25 | >32 | |
| 47 | ND | 9.07 | 11.6 | >32 | 106 |
| 48 | ~100 | 10.15 | 4.1 | >32 | |

[a]DISCOVERX β-arrestin PATHHUNTER assay (n = 3).
[b]High content imaging based β-arrestin translocation assay (n = 2).

Replacement of the pyridyl and furan/thiophene side chains was also briefly investigated and the compounds screened in the DISCOVERX KOR assay.

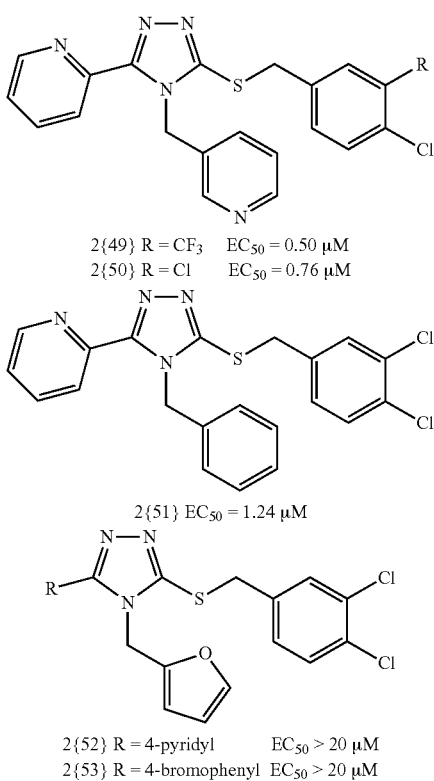

2{49} R = CF₃  EC₅₀ = 0.50 μM
2{50} R = Cl   EC₅₀ = 0.76 μM

2{51} EC₅₀ = 1.24 μM

2{52} R = 4-pyridyl      EC₅₀ > 20 μM
2{53} R = 4-bromophenyl  EC₅₀ > 20 μM

The pyridyl side chain appeared to be critical to the potency, however the furan/thiophene was successfully replaced with other aromatic moieties without detriment to the potency. These limited examples indicate that the core scaffold can tolerate an expanded range of diverse functionality and opens up several additional structural elements to exploration.

Example 8

Pharmacology and ADMET Properties of Declared Agonist Probe Compound

As a representative of the Chemotype II series, the MLPCN probe molecule 2{8} was subjected to a binding assay panel of 44 GPCR and other molecular targets by the Psychoactive Drug Screening Program (PDSP)(Table 10). The compound was initially screened in a radioligand binding assay at a constant concentration (10 μM) to identify possible activity of the compound. Results showing significant activity in the initial screen were selected for $K_i$ determinations.

TABLE 10

| GCPR | $K_i$ (nM) | GCPR | $K_i$ (nM) |
| --- | --- | --- | --- |
| 5ht1a | X | D2 | X |
| 5ht1b | X | D3 | X |
| 5ht1d | X | D4 | X |
| 5ht1e | X | D5 | 7018 |
| 5ht2a | 3788 | DAT | X |
| 5ht2b | 1237 | DOR | 5351[a] |
| 5ht2c | X | GabaA | X |
| 5ht3 | X | H1 | X |
| 5ht5a | 4986 | H2 | X |
| 5ht6 | X | H3 | X |

TABLE 10-continued

| GCPR | $K_i$ (nM) | GCPR | $K_i$ (nM) |
| --- | --- | --- | --- |
| 5ht7 | X | H4 | X |
| Alpha1A | X | KOR | 2.4[a] |
| Alpha1B | X | M1 | X |
| Alpha1D | X | M2 | X |
| Alpha2A | X | M3 | X |
| Alpha2B | 5525 | M4 | X |
| Alpha2C | 9601 | M5 | 4418 |
| Beta1 | X | MOR | 1900[a] |
| Beta2 | X | NET | 5870 |
| Beta3 | 7312 | SERT | X |
| BZP Rat Brain Site | X | Sigma1 | X |
| D1 | 1796 | Sigma2 | 2905 |

X, $K_i$ >10,000 nM or missed in primary screen.
[a]Average of separate $K_i$ determinations.

Although modestly more potent analogues were subsequently found, this selectivity data was representative of this series. The test compound was found to possess weak binding affinity for 11 nonopioid targets with $K_i$ values in the 1 to 10 μM range. In contrast, the binding affinity for the KOR was at least 500-fold more potent ($K_i$=2.4 nM). The compound was found to possess a KOR:DOR selectivity ratio of over 1:2,000 and a KOR:MOR selectivity ratio of 1:792 in the secondary binding assays. However, the binding affinity values did not correlate with the functional assay data (EC₅₀=870 nM).

In addition to profiling the selectivity of compound 2{8}, the basic physical properties were also assessed. This analysis indicated that the solubility of compound 2{8} in aqueous buffer was <0.1 μg/mL at pH 5.0, 0.29 μg/mL at pH 6.2, and 0.14 μg/mL at pH 7.4. In the PAMPA screen (Kansy, et al. (1998) J. Med. Chem. 41:1007-1010; donor compartment pH's 5.0/6.2/7.4; acceptor compartment pH 7.4), compound 2{8} have excellent permeability (1793×10⁻⁶ cm/s at pH 5.0; 1921×10⁻⁶ cm/s at pH 6.2; and 2089×10⁻⁶ cm/s at pH 7.4). Furthermore, compound 2{8} had almost 3-fold selectivity in the blood brain barrier (BBB-Pe) PAMPA assay (242×10⁻⁶ cm/s in aqueous buffer; donor and acceptor compartments both at pH 7.4). This agonist probe was also determined to be highly bound (>99%) to both human and mouse plasma. Moreover, this compound showed excellent stability (100% remaining at 3 hours) in both human and mouse plasma and was rapidly metabolized in either human or mouse microsomes (0.03% remaining after 1 hour). In addition, the LC₅₀ value of 2{8} toward Fa2N-4 immortalized human hepatocytes was >50 μM.

G protein coupling assays using a ³⁵S-GTPγS binding assay were undertaken to demonstrate single point efficacy for the compound 2{8}. Compound 2{8} was found to be a potent inhibitor of the ³⁵S-GTPγS coupling (EC₅₀=55.2±11.8 nM; $E_{max}$ 101±10%), indicating a direct functional effect on G-coupling. Potency was comparable to the β-arrestin translocation HCS assay.

Since agonists can differentially activate GPCRs to engage diverse signaling cascades, a secondary, downstream MAP kinase assay (Erk1/2 activation) was used to evaluate agonist activity. Single point efficacy curves revealed a tendency for compound 2{8} to be more efficacious in this assay (EC₅₀=520±36.8 nM, p<0.001 agonist vs. U69593; $E_{max}$ 145±8%, p<0.01 agonist vs. U69593).

Example 9

Analysis of Additional Chemotype II Compounds

Additional triazole analogues were prepared and analyzed in a β-arrestin recruitment assay. The analogs analogue and their activity are listed in Table 11.

TABLE 11

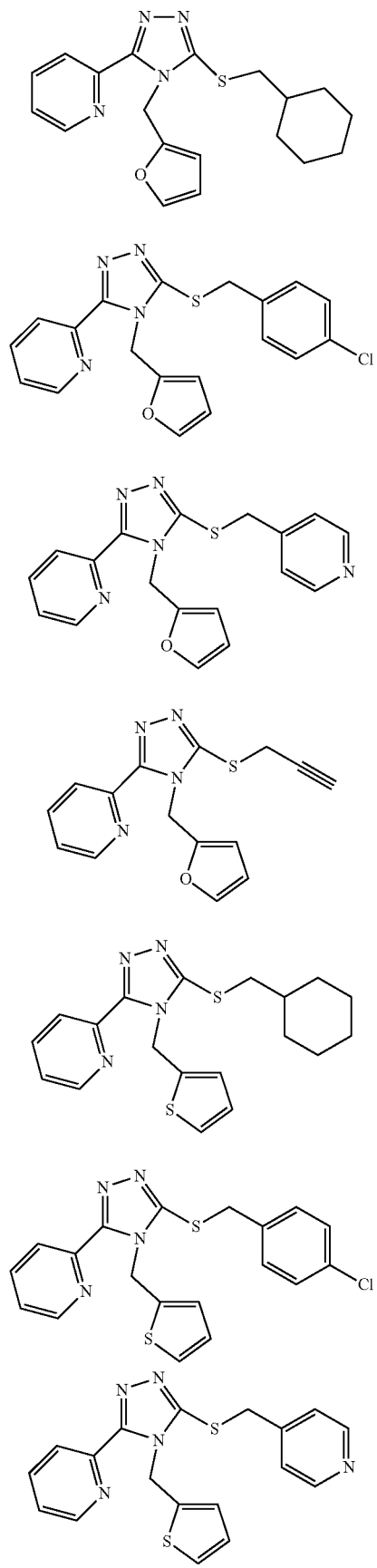

| Entry | R¹ | R² | R³ | Potency, $EC_{50}$ (DRx[a], μM) |
|---|---|---|---|---|
| 1 | 2-pyridyl | 4-methoxyphenyl | phenyl | >20 |
| 2 | 2-pyridyl | 4-methoxyphenyl | 4-bromophenyl | >20 |
| 3 | 2-pyridyl | 4-methoxyphenyl | 3,4-dichlorophenyl | 11.80 |
| 4 | 2-pyridyl | 4-methoxyphenyl | 4-chloro-3-triflouoromethylphenyl | >19.7 |
| 5 | 2-pyridyl | phenyl | phenyl | >20 |
| 6 | 2-pyridyl | phenyl | 4-bromophenyl | 4.06 |
| 7 | 2-pyridyl | phenyl | 3,4-dichlorophenyl | 1.24 |
| 8 | 2-pyridyl | phenyl | 4-chloro-3-triflouoromethylphenyl | 2.22 |
| 9 | 2-pyridyl | 3-pyridyl | phenyl | >20 |
| 10 | 2-pyridyl | 3-pyridyl | 4-bromophenyl | 8.51 |
| 11 | 2-pyridyl | 3-pyridyl | 3,4-dichlorophenyl | 0.76 |
| 12 | 2-pyridyl | 3-pyridyl | 4-chloro-3-triflouoromethylphenyl | 0.50 |
| 13 | 2-pyridyl | 2-chlorophenyl | phenyl | >20 |
| 14 | 2-pyridyl | 2-chlorophenyl | 4-bromophenyl | 14.23 |
| 15 | 2-pyridyl | 2-chlorophenyl | 3,4-dichlorophenyl | 11.80 |
| 16 | 2-pyridyl | 2-chlorophenyl | 4-chloro-3-triflouoromethylphenyl | 4.30 |
| 17 | 4-pyridyl | 2-furyl | phenyl | >20 |
| 18 | 4-pyridyl | 2-furyl | 4-bromophenyl | >20 |
| 19 | 4-pyridyl | 2-furyl | 3,4-dichlorophenyl | >20 |
| 20 | 4-pyridyl | 2-furyl | 4-chloro-3-triflouoromethylphenyl | >20 |
| 21 | 4-bromophenyl | 2-furyl | phenyl | >20 |
| 22 | 4-bromophenyl | 2-furyl | 4-bromophenyl | 13.48 |
| 23 | 4-bromophenyl | 2-furyl | 3,4-dichlorophenyl | 11.00 |
| 24 | 4-bromophenyl | 2-furyl | 4-chloro-3-triflouoromethylphenyl | 13.28 |

[a]DISCOVERX β-arrestin PATHHUNTER assay (n = 4)

While the potency in the β-arrestin recruitment assay for many of these compounds was not as good as other compounds described herein, experiments with other members of this chemotype indicate that these compounds may have a surprisingly high affinity for the KOR and/or modulate distinct KOR signaling pathway. Therefore, these compounds, as well as those listed below, may be of use in modulating the kappa opioid receptor.

-continued
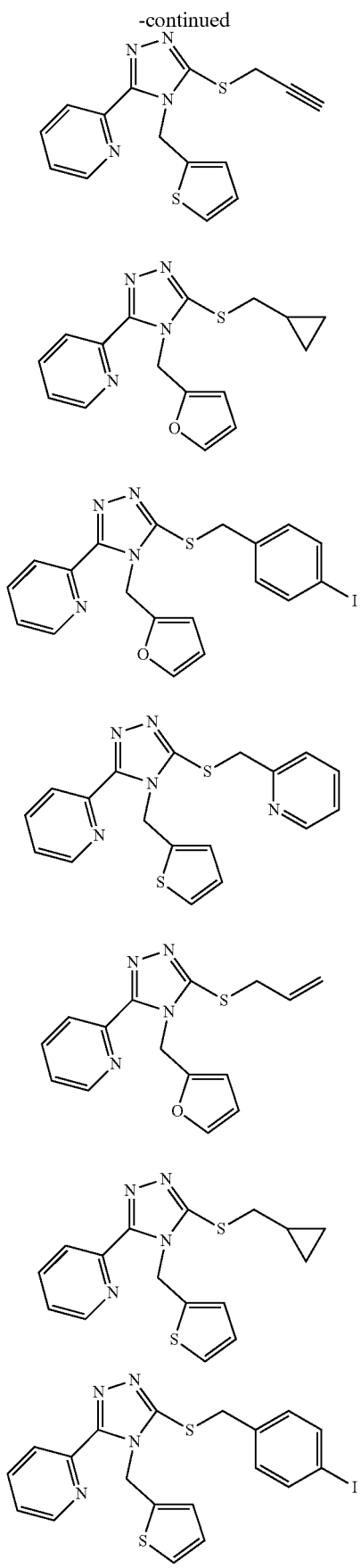
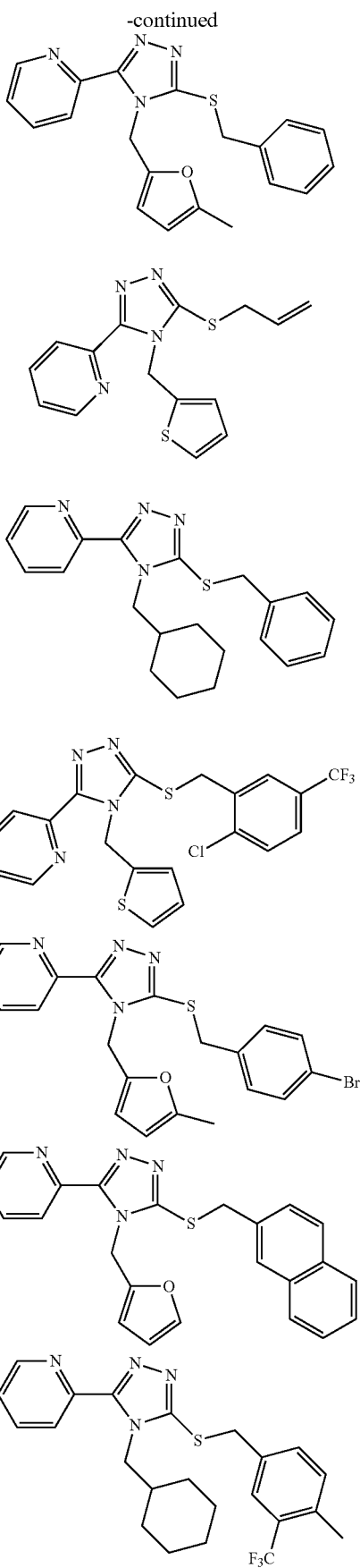

-continued
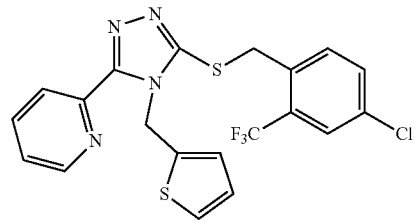
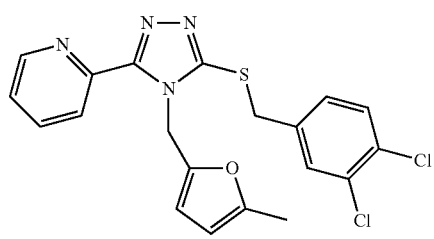
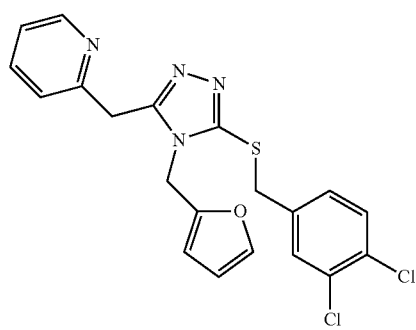
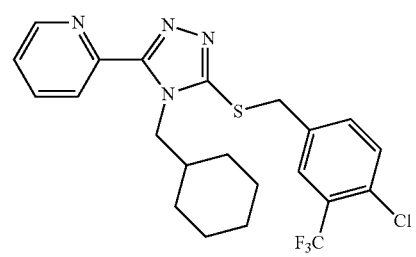
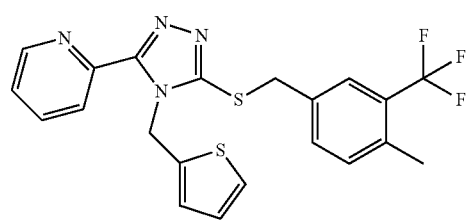
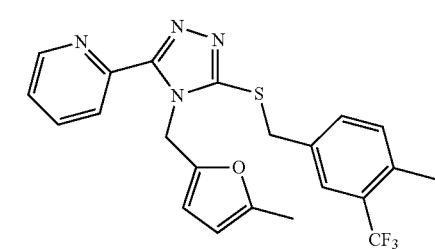
-continued
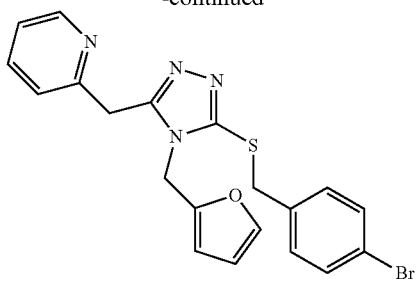
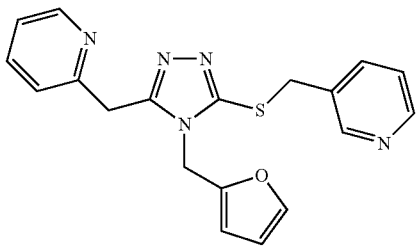
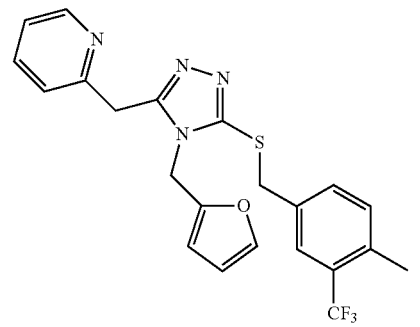
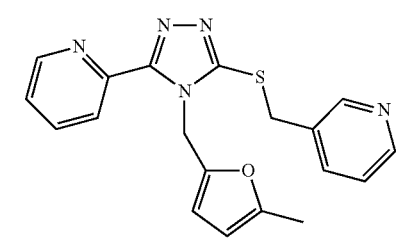
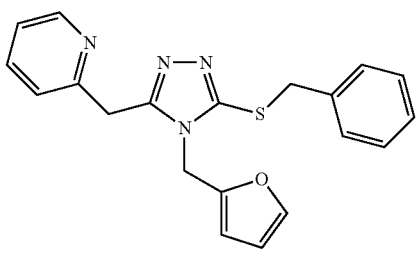
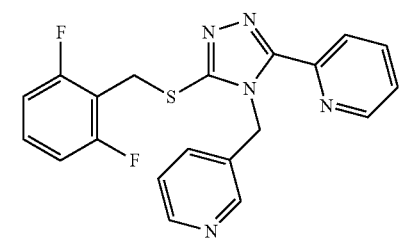

-continued

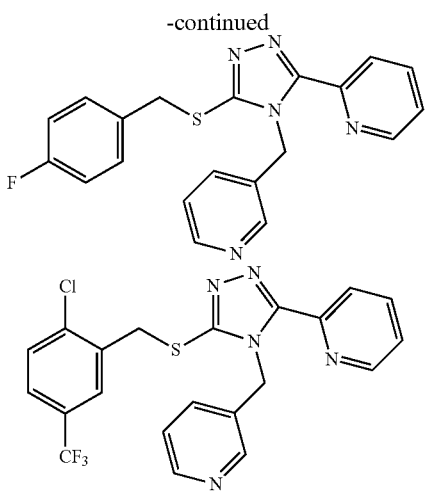

Example 10

Plasma and Brain Concentrations Chemotype II Compounds

Compounds KUIP10051N and KUC104186N (compound 2{41}) were prepared in a vehicle composed of 10% DMSO (dimethylsulfoxide) and 10% TWEEN 80 in water and were administered intraperitoneally (i.p.) at a dose of 10 mg/kg (injection volume of 10 μL/mg mouse body weight).

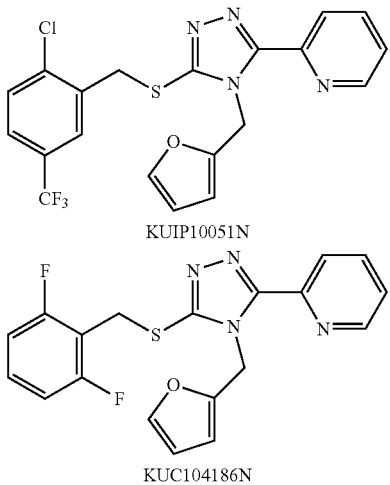

KUIP10051N

KUC104186N

Figure 1B:
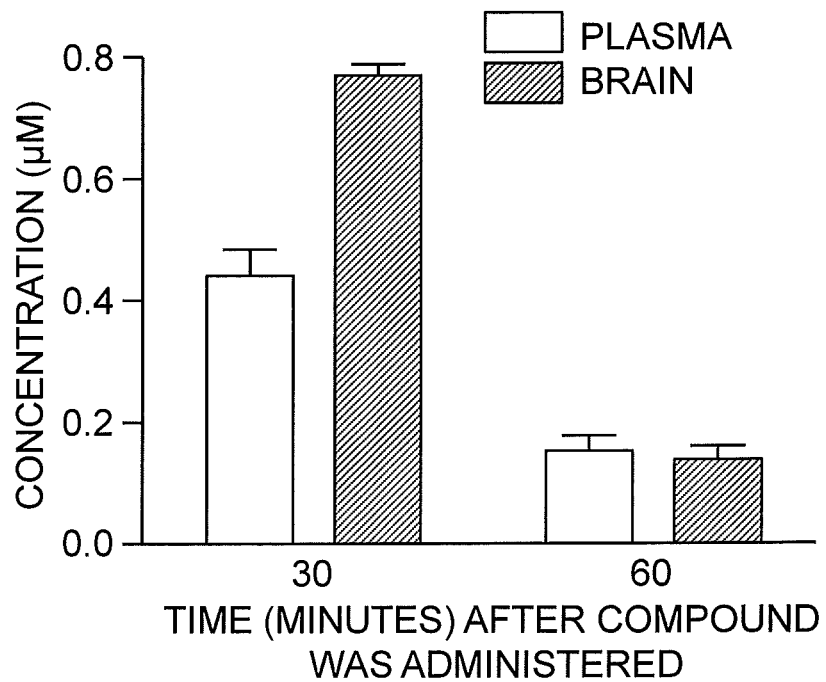

Adult male C57BL/6 mice from Jackson Labs were used (age ~2 months). Plasma and brains were collected at 30 and 60 minutes from two groups of mice (n=3). One mouse was excluded from the 30 minute time point for KUIP104186N due to mis-injection. Isolated plasma and whole brain homogenates were subject to analysis using LC/MS. Concentrations were determined from standard curves prepared in the appropriate matrix and are presented in FIG. 1A and FIG. 1B.

What is claimed is:

1. A compound of Formula I or Formula II:

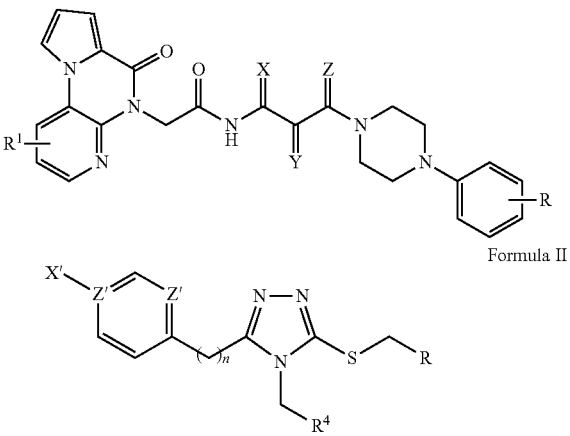

wherein

X, Y and Z are independently selected from H, H; O; S or NH;

$R^1$ is H, a halogen group or a substituted or unsubstituted lower alkyl or alkoxy group, wherein the substituents on the lower alkyl or alkoxy group are selected from the group consisting of halogen, lower alkyl, lower alkoxy, alkenyl, hydroxyl, amino, nitro, nitroso, carboxyl, sulhydryl, oxo, —$CF_3$, and —CN;

$R^2$ is a substituent on one or more ring atoms and is for each ring atom independently H, a halogen group, or a substituted or unsubstituted lower alkyl or alkoxy group, wherein the substituents on the lower alkyl and alkoxy are selected from the group consisting of halogen, lower alkyl, lower alkoxy, alkenyl, hydroxyl, amino, nitro, nitroso, carboxyl, sulhydryl, oxo, —$CF_3$, and —CN;

X' is hydrogen or Br;

one Z' is N and the other Z' is C, CH or N;

n is 0 or 1;

$R^3$ is naphthyl; cycloalkyl; —C≡CH; —C=$CH_2$; phenyl with two or more substituents independently selected from the group of lower alkyl, lower alkoxy, alkenyl, hydroxyl, amino, iodo, nitro, nitroso, carboxyl, sulhydryl, —$CF_3$, and —CN; or phenyl substituted with a trifluoromethyl group and a halogen or alkyl group; and $R^4$ is aryl, substituted aryl, heteroaryl, substituted heteroaryl or cycloalkyl, wherein the heteroaryl or substituted heteroaryl is a 5- or 6-membered aromatic ring with at least one heteroatom selected from the group of N, O or S; and substituted aryl or substituted heteroaryl comprises one or more substituents selected from the group of halogen, lower alkyl, lower alkoxy, alkenyl, hydroxyl, amino, nitro, nitroso, carboxyl, sulhydryl, —$CF_3$, and —CN.

2. The compound of claim 1, wherein $R^4$ is 2-furyl, 2-thiophene or 3-pyridyl.

* * * * *